(12) United States Patent
Barachant

(10) Patent No.: US 10,905,383 B2
(45) Date of Patent: Feb. 2, 2021

(54) METHODS AND APPARATUS FOR UNSUPERVISED ONE-SHOT MACHINE LEARNING FOR CLASSIFICATION OF HUMAN GESTURES AND ESTIMATION OF APPLIED FORCES

(71) Applicant: Facebook Technologies, LLC, Menlo Park, CA (US)

(72) Inventor: Alexandre Barachant, Brooklyn, NY (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

(21) Appl. No.: 16/288,880

(22) Filed: Feb. 28, 2019

(65) Prior Publication Data

US 2020/0275895 A1    Sep. 3, 2020

(51) Int. Cl.
*A61B 5/00*    (2006.01)
*G06N 20/00*    (2019.01)
(Continued)

(52) U.S. Cl.
CPC .......... *A61B 5/7267* (2013.01); *A61B 5/0488* (2013.01); *A61B 5/1107* (2013.01);
(Continued)

(58) Field of Classification Search
CPC ... A61B 5/7267; A61B 5/0488; A61B 5/1107; A61B 5/6824; A61B 5/6831; A61B 8/08; G06N 20/00
See application file for complete search history.

(56) References Cited

U.S. PATENT DOCUMENTS

| 4,055,168 A | 10/1977 | Miller et al. |
| 4,896,120 A | 1/1990 | Kamil |

(Continued)

FOREIGN PATENT DOCUMENTS

| CA | 2902045 A1 | 8/2014 |
| CA | 2921954 A1 | 2/2015 |

(Continued)

OTHER PUBLICATIONS

Gopura, R. A. R. C., and Kazuo Kiguchi. "A human forearm and wrist motion assist exoskeleton robot with EMG-based fuzzy-neuro control." In 2008 2nd IEEE RAS & EMBS International Conference on Biomedical Robotics and Biomechatronics, pp. 550-555. IEEE, 2008. (Year: 2008).*

(Continued)

*Primary Examiner* — Vincent Gonzales
*Assistant Examiner* — Casey R. Garner
(74) *Attorney, Agent, or Firm* — FisherBroyles, LLP

(57) ABSTRACT

Methods and apparatus for training a classification model and using the trained classification model to recognize gestures performed by a user. An apparatus comprises a processor that is programmed to: receive, via a plurality of neuromuscular sensors, a first plurality of neuromuscular signals from a user as the user performs a first single act of a gesture; train a classification model based on the first plurality of neuromuscular signals, the training including: deriving value(s) from the first plurality of neuromuscular signals, the value(s) indicative of distinctive features of the gesture including at least one feature that linearly varies with a force applied during performance of the gesture; and generating a first categorical representation of the gesture in the classification model based on the value(s); and determine that the user performed a second single act of the gesture, (Continued)

based on the trained classification model and a second plurality of neuromuscular signals.

30 Claims, 17 Drawing Sheets

(51) Int. Cl.
  *A61B 5/0488* (2006.01)
  *A61B 5/11* (2006.01)
  *A61B 8/08* (2006.01)

(52) U.S. Cl.
  CPC .......... *A61B 5/6824* (2013.01); *A61B 5/6831* (2013.01); *A61B 8/08* (2013.01); *G06N 20/00* (2019.01)

(56) References Cited

U.S. PATENT DOCUMENTS

| | | | |
|---|---|---|---|
| 5,625,577 | A | 4/1997 | Kunii et al. |
| 6,005,548 | A | 12/1999 | Latypov et al. |
| 6,009,210 | A | 12/1999 | Kand |
| 6,244,873 | B1 | 6/2001 | Hill et al. |
| 6,411,843 | B1 | 6/2002 | Zarychta |
| 6,658,287 | B1 | 12/2003 | Litt et al. |
| 6,720,984 | B1 | 4/2004 | Jorgensen et al. |
| 6,774,885 | B1 | 8/2004 | Even-Zohar |
| 6,942,621 | B2 | 9/2005 | Avinash et al. |
| 7,089,148 | B1 | 8/2006 | Bachmann et al. |
| 7,351,975 | B2 | 4/2008 | Brady et al. |
| 7,574,253 | B2 | 8/2009 | Edney et al. |
| 7,580,742 | B2 | 8/2009 | Tan et al. |
| 7,787,946 | B2 | 8/2010 | Stahmann et al. |
| 7,805,386 | B2 | 9/2010 | Greer |
| 7,901,368 | B2 | 3/2011 | Flaherty et al. |
| 8,170,656 | B2 | 5/2012 | Tan et al. |
| 8,190,249 | B1 | 5/2012 | Gharieb et al. |
| 8,311,623 | B2 | 11/2012 | Sanger |
| 8,351,651 | B2 | 1/2013 | Lee |
| 8,421,634 | B2 | 4/2013 | Tan et al. |
| 8,435,191 | B2 | 5/2013 | Barboutis et al. |
| 8,437,844 | B2 | 5/2013 | Syed Momen et al. |
| 8,447,704 | B2 | 5/2013 | Tan et al. |
| 8,484,022 | B1 | 7/2013 | Vanhoucke |
| 8,718,980 | B2 | 5/2014 | Garudadri et al. |
| 8,744,543 | B2 | 6/2014 | Li et al. |
| 8,754,862 | B2 | 6/2014 | Zaliva |
| D717,685 | S | 11/2014 | Bailey et al. |
| 8,880,163 | B2 | 11/2014 | Barachant et al. |
| 8,890,875 | B2 | 11/2014 | Jammes et al. |
| 8,892,479 | B2 | 11/2014 | Tan et al. |
| 9,037,530 | B2 | 5/2015 | Tan et al. |
| D742,272 | S | 11/2015 | Bailey et al. |
| 9,218,574 | B2 | 12/2015 | Phillipps et al. |
| 9,235,934 | B2 | 1/2016 | Mandella et al. |
| 9,240,069 | B1 | 1/2016 | Li |
| 9,278,453 | B2 | 3/2016 | Assad |
| 9,299,248 | B2 | 3/2016 | Lake et al. |
| D756,359 | S | 5/2016 | Bailey et al. |
| 9,351,653 | B1 | 5/2016 | Harrison |
| 9,367,139 | B2 | 6/2016 | Ataee et al. |
| 9,372,535 | B2 | 6/2016 | Bailey et al. |
| 9,389,694 | B2 | 7/2016 | Ataee et al. |
| 9,408,316 | B2 | 8/2016 | Bailey et al. |
| 9,459,697 | B2 | 10/2016 | Bedikian et al. |
| 9,483,123 | B2 | 11/2016 | Aleem et al. |
| 9,597,015 | B2 | 3/2017 | McNames et al. |
| 9,600,030 | B2 | 3/2017 | Bailey et al. |
| 9,612,661 | B2 * | 4/2017 | Wagner .................. G06F 3/016 |
| 9,613,262 | B2 | 4/2017 | Holz |
| 9,654,477 | B1 | 5/2017 | Kotamraju |
| 9,659,403 | B1 | 5/2017 | Horowitz |
| 9,687,168 | B2 | 6/2017 | John |
| 9,696,795 | B2 | 7/2017 | Marcolina et al. |
| 9,720,515 | B2 | 8/2017 | Wagner et al. |
| 9,741,169 | B1 | 8/2017 | Holz |
| 9,766,709 | B2 | 9/2017 | Holz |
| 9,785,247 | B1 | 10/2017 | Horowitz et al. |
| 9,788,789 | B2 | 10/2017 | Bailey |
| 9,864,431 | B2 | 1/2018 | Keskin et al. |
| 9,867,548 | B2 | 1/2018 | Le et al. |
| 9,880,632 | B2 | 1/2018 | Ataee et al. |
| 9,891,718 | B2 | 2/2018 | Connor |
| 10,042,422 | B2 | 8/2018 | Morun et al. |
| 10,070,799 | B2 | 9/2018 | Ang et al. |
| 10,078,435 | B2 | 9/2018 | Noel |
| 10,101,809 | B2 | 10/2018 | Morun et al. |
| 10,152,082 | B2 | 12/2018 | Bailey |
| 10,188,309 | B2 | 1/2019 | Morun et al. |
| 10,199,008 | B2 | 2/2019 | Aleem et al. |
| 10,203,751 | B2 | 2/2019 | Keskin et al. |
| 10,216,274 | B2 | 2/2019 | Chapeskie et al. |
| 10,251,577 | B2 | 4/2019 | Morun et al. |
| 10,310,601 | B2 | 6/2019 | Morun et al. |
| 10,331,210 | B2 | 6/2019 | Morun et al. |
| 10,362,958 | B2 | 7/2019 | Morun et al. |
| 10,409,371 | B2 | 9/2019 | Kaifosh et al. |
| 10,437,335 | B2 | 10/2019 | Daniels |
| 10,460,455 | B2 | 10/2019 | Giurgica-Tiron et al. |
| 10,489,986 | B2 | 11/2019 | Kaifosh et al. |
| 10,496,168 | B2 | 12/2019 | Kaifosh et al. |
| 10,504,286 | B2 | 12/2019 | Kaifosh et al. |
| 2003/0144829 | A1 | 7/2003 | Geatz et al. |
| 2003/0171921 | A1 | 9/2003 | Manabe et al. |
| 2003/0184544 | A1 | 10/2003 | Prudent |
| 2004/0054273 | A1 | 3/2004 | Finneran et al. |
| 2004/0092839 | A1 | 5/2004 | Shin et al. |
| 2006/0129057 | A1 | 6/2006 | Maekawa et al. |
| 2007/0009151 | A1 | 1/2007 | Pittman et al. |
| 2007/0172797 | A1 | 7/2007 | Hada et al. |
| 2007/0177770 | A1 | 8/2007 | Derchak et al. |
| 2007/0256494 | A1 | 11/2007 | Nakamura et al. |
| 2007/0285399 | A1 | 12/2007 | Lund |
| 2008/0051673 | A1 | 2/2008 | Kong et al. |
| 2008/0052643 | A1 | 2/2008 | Ike et al. |
| 2008/0091121 | A1 * | 4/2008 | Sun .................. A61B 5/0059 600/587 |
| 2008/0103639 | A1 | 5/2008 | Troy et al. |
| 2008/0214360 | A1 | 9/2008 | Stirling et al. |
| 2008/0221487 | A1 | 9/2008 | Zohar et al. |
| 2009/0027337 | A1 | 1/2009 | Hildreth |
| 2009/0079813 | A1 | 3/2009 | Hildreth |
| 2009/0082692 | A1 | 3/2009 | Hale et al. |
| 2009/0082701 | A1 | 3/2009 | Zohar et al. |
| 2009/0112080 | A1 | 4/2009 | Matthews |
| 2009/0124881 | A1 | 5/2009 | Rytky |
| 2009/0326406 | A1 | 12/2009 | Tan et al. |
| 2009/0327171 | A1 | 12/2009 | Tan et al. |
| 2010/0030532 | A1 | 2/2010 | Arora et al. |
| 2010/0063794 | A1 | 3/2010 | Hernandez-Rebollar |
| 2010/0106044 | A1 | 4/2010 | Linderman |
| 2010/0113910 | A1 | 5/2010 | Brauers et al. |
| 2010/0280628 | A1 | 11/2010 | Sankai |
| 2010/0292595 | A1 | 11/2010 | Paul |
| 2010/0292606 | A1 | 11/2010 | Prakash et al. |
| 2010/0292617 | A1 | 11/2010 | Lei et al. |
| 2010/0293115 | A1 | 11/2010 | Seyed Momen |
| 2010/0315266 | A1 | 12/2010 | Gunawardana et al. |
| 2011/0077484 | A1 | 3/2011 | Van Slyke et al. |
| 2011/0092826 | A1 | 4/2011 | Lee et al. |
| 2011/0173204 | A1 | 7/2011 | Murillo et al. |
| 2011/0173574 | A1 | 7/2011 | Clavin et al. |
| 2011/0230782 | A1 | 9/2011 | Bartol et al. |
| 2012/0066163 | A1 | 3/2012 | Balls et al. |
| 2012/0188158 | A1 | 7/2012 | Tan et al. |
| 2012/0265480 | A1 | 10/2012 | Oshima |
| 2012/0283526 | A1 | 11/2012 | Gommesen et al. |
| 2013/0004033 | A1 | 1/2013 | Trugenberger |
| 2013/0077820 | A1 | 3/2013 | Marais et al. |
| 2013/0123656 | A1 | 5/2013 | Heck |
| 2013/0141375 | A1 | 6/2013 | Ludwig et al. |
| 2013/0207889 | A1 | 8/2013 | Chang et al. |
| 2013/0217998 | A1 | 8/2013 | Mahfouz et al. |

(56) References Cited

U.S. PATENT DOCUMENTS

| | | |
|---|---|---|
| 2013/0232095 A1* | 9/2013 | Tan .................. G06F 3/015 706/12 |
| 2013/0317382 A1 | 11/2013 | Le |
| 2013/0317648 A1 | 11/2013 | Assad |
| 2014/0052150 A1 | 2/2014 | Taylor et al. |
| 2014/0092009 A1 | 4/2014 | Yen et al. |
| 2014/0098018 A1 | 4/2014 | Kim et al. |
| 2014/0196131 A1 | 7/2014 | Lee |
| 2014/0198034 A1 | 7/2014 | Bailey et al. |
| 2014/0198035 A1 | 7/2014 | Bailey et al. |
| 2014/0223462 A1 | 8/2014 | Aimone et al. |
| 2014/0240103 A1 | 8/2014 | Lake et al. |
| 2014/0240223 A1 | 8/2014 | Lake et al. |
| 2014/0245200 A1 | 8/2014 | Holz |
| 2014/0249397 A1 | 9/2014 | Lake et al. |
| 2014/0277622 A1 | 9/2014 | Raniere |
| 2014/0278441 A1 | 9/2014 | Ton et al. |
| 2014/0297528 A1 | 10/2014 | Agrawal et al. |
| 2014/0304665 A1 | 10/2014 | Holz |
| 2014/0330404 A1 | 11/2014 | Abdelghani et al. |
| 2014/0334083 A1 | 11/2014 | Bailey |
| 2014/0344731 A1 | 11/2014 | Holz |
| 2014/0355825 A1 | 12/2014 | Kim et al. |
| 2014/0358024 A1 | 12/2014 | Nelson et al. |
| 2014/0361988 A1 | 12/2014 | Katz et al. |
| 2014/0364703 A1 | 12/2014 | Kim et al. |
| 2014/0365163 A1 | 12/2014 | Jallon |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0025355 A1 | 1/2015 | Bailey et al. |
| 2015/0029092 A1 | 1/2015 | Holz et al. |
| 2015/0035827 A1 | 2/2015 | Yamaoka et al. |
| 2015/0045689 A1 | 2/2015 | Barone |
| 2015/0045699 A1 | 2/2015 | Mokaya et al. |
| 2015/0051470 A1 | 2/2015 | Bailey et al. |
| 2015/0057770 A1 | 2/2015 | Bailey et al. |
| 2015/0070270 A1 | 3/2015 | Bailey et al. |
| 2015/0070274 A1 | 3/2015 | Morozov |
| 2015/0084860 A1 | 3/2015 | Aleem et al. |
| 2015/0109202 A1 | 4/2015 | Ataee et al. |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1 | 5/2015 | Morun et al. |
| 2015/0157944 A1 | 6/2015 | Gottlieb |
| 2015/0169074 A1 | 6/2015 | Ataee et al. |
| 2015/0182165 A1 | 7/2015 | Miller et al. |
| 2015/0193949 A1 | 7/2015 | Katz et al. |
| 2015/0223716 A1 | 8/2015 | Korkala et al. |
| 2015/0234426 A1 | 8/2015 | Bailey et al. |
| 2015/0261306 A1 | 9/2015 | Lake |
| 2015/0261318 A1 | 9/2015 | Scavezze et al. |
| 2015/0277575 A1 | 10/2015 | Ataee et al. |
| 2015/0296553 A1 | 10/2015 | DiFranco et al. |
| 2015/0302168 A1 | 10/2015 | De Sapio et al. |
| 2015/0309563 A1 | 10/2015 | Connor |
| 2015/0309582 A1 | 10/2015 | Gupta |
| 2015/0313496 A1 | 11/2015 | Connor |
| 2015/0325202 A1 | 11/2015 | Lake et al. |
| 2015/0332013 A1 | 11/2015 | Lee et al. |
| 2015/0346701 A1 | 12/2015 | Gordon et al. |
| 2015/0366504 A1 | 12/2015 | Connor |
| 2015/0370326 A1 | 12/2015 | Chapeskie et al. |
| 2015/0370333 A1 | 12/2015 | Ataee et al. |
| 2016/0011668 A1 | 1/2016 | Gilad-Bachrach et al. |
| 2016/0049073 A1* | 2/2016 | Lee .................. G08C 23/04 340/12.5 |
| 2016/0092504 A1 | 3/2016 | Mitri et al. |
| 2016/0144172 A1 | 5/2016 | Hsueh et al. |
| 2016/0162604 A1 | 6/2016 | Xiaoli et al. |
| 2016/0187992 A1 | 6/2016 | Yamamoto et al. |
| 2016/0235323 A1 | 8/2016 | Tadi et al. |
| 2016/0239080 A1 | 8/2016 | Marcolina et al. |
| 2016/0262687 A1 | 9/2016 | Imperial |
| 2016/0274758 A1 | 9/2016 | Bailey |
| 2016/0275726 A1 | 9/2016 | Mullins |
| 2016/0292497 A1 | 10/2016 | Kehtarnavaz et al. |
| 2016/0313798 A1 | 10/2016 | Connor |
| 2016/0313801 A1 | 10/2016 | Wagner et al. |
| 2016/0313890 A1 | 10/2016 | Walline et al. |
| 2016/0313899 A1 | 10/2016 | Noel |
| 2016/0350973 A1 | 12/2016 | Shapira et al. |
| 2017/0031502 A1 | 2/2017 | Rosenberg et al. |
| 2017/0035313 A1 | 2/2017 | Hong et al. |
| 2017/0061817 A1 | 3/2017 | Mettler May |
| 2017/0068445 A1 | 3/2017 | Lee et al. |
| 2017/0080346 A1 | 3/2017 | Abbas |
| 2017/0090604 A1 | 3/2017 | Barbier |
| 2017/0091567 A1 | 3/2017 | Wang et al. |
| 2017/0119472 A1 | 5/2017 | Herrmann et al. |
| 2017/0123487 A1 | 5/2017 | Hazra et al. |
| 2017/0124816 A1 | 5/2017 | Yang et al. |
| 2017/0161635 A1 | 6/2017 | Oono et al. |
| 2017/0188980 A1 | 7/2017 | Ash |
| 2017/0259167 A1 | 9/2017 | Cook et al. |
| 2017/0285756 A1 | 10/2017 | Wang et al. |
| 2017/0285848 A1* | 10/2017 | Rosenberg ............ G06F 3/0202 |
| 2017/0296363 A1* | 10/2017 | Yetkin .................. A61F 2/72 |
| 2017/0301630 A1 | 10/2017 | Nguyen et al. |
| 2017/0308118 A1 | 10/2017 | Ito |
| 2017/0344706 A1 | 11/2017 | Torres et al. |
| 2017/0347908 A1 | 12/2017 | Watanabe et al. |
| 2018/0000367 A1 | 1/2018 | Longinotti-Buitoni |
| 2018/0020951 A1* | 1/2018 | Kaifosh ................ A61B 5/0488 607/48 |
| 2018/0020978 A1 | 1/2018 | Kaifosh et al. |
| 2018/0024634 A1 | 1/2018 | Kaifosh et al. |
| 2018/0024635 A1 | 1/2018 | Kaifosh et al. |
| 2018/0064363 A1 | 3/2018 | Morun et al. |
| 2018/0067553 A1 | 3/2018 | Morun et al. |
| 2018/0081439 A1 | 3/2018 | Daniels |
| 2018/0088765 A1 | 3/2018 | Bailey |
| 2018/0092599 A1 | 4/2018 | Kerth et al. |
| 2018/0095630 A1 | 4/2018 | Bailey |
| 2018/0101235 A1 | 4/2018 | Bodensteiner et al. |
| 2018/0101289 A1 | 4/2018 | Bailey |
| 2018/0120948 A1 | 5/2018 | Aleem et al. |
| 2018/0140441 A1* | 5/2018 | Poirters .................. A61F 2/54 |
| 2018/0150033 A1 | 5/2018 | Lake et al. |
| 2018/0153430 A1* | 6/2018 | Ang .................. A61B 5/0488 |
| 2018/0153444 A1 | 6/2018 | Yang et al. |
| 2018/0154140 A1 | 6/2018 | Bouton et al. |
| 2018/0178008 A1 | 6/2018 | Bouton et al. |
| 2018/0301057 A1* | 10/2018 | Hargrove ............ G16H 20/30 |
| 2018/0307314 A1 | 10/2018 | Connor |
| 2018/0321745 A1 | 11/2018 | Morun et al. |
| 2018/0321746 A1 | 11/2018 | Morun et al. |
| 2018/0333575 A1 | 11/2018 | Bouton |
| 2018/0344195 A1 | 12/2018 | Morun et al. |
| 2018/0360379 A1 | 12/2018 | Harrison et al. |
| 2019/0008453 A1 | 1/2019 | Spoof |
| 2019/0025919 A1 | 1/2019 | Tadi et al. |
| 2019/0033967 A1 | 1/2019 | Morun et al. |
| 2019/0033974 A1 | 1/2019 | Mu et al. |
| 2019/0038166 A1 | 2/2019 | Tavabi et al. |
| 2019/0076716 A1 | 3/2019 | Chiou et al. |
| 2019/0121305 A1* | 4/2019 | Kaifosh .................. G05B 13/048 |
| 2019/0121306 A1 | 4/2019 | Kaifosh et al. |
| 2019/0146809 A1 | 5/2019 | Lee et al. |
| 2019/0150777 A1 | 5/2019 | Guo et al. |
| 2019/0192037 A1 | 6/2019 | Morun et al. |
| 2019/0212817 A1 | 7/2019 | Kaifosh et al. |
| 2019/0223748 A1 | 7/2019 | Al-natsheh et al. |
| 2019/0227627 A1 | 7/2019 | Kaifosh et al. |
| 2019/0228330 A1 | 7/2019 | Kaifosh et al. |
| 2019/0228533 A1 | 7/2019 | Giurgica-Tiron et al. |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |
| 2019/0247650 A1 | 8/2019 | Tran |
| 2019/0324549 A1 | 10/2019 | Araki et al. |
| 2019/0357787 A1 | 11/2019 | Barachant et al. |
| 2019/0362557 A1 | 11/2019 | Lacey et al. |

(56) References Cited

U.S. PATENT DOCUMENTS

FOREIGN PATENT DOCUMENTS

| | | |
|---|---|---|
| CA | 2939644 A1 | 8/2015 |
| CN | 1838933 A | 9/2006 |
| CN | 103777752 A | 5/2014 |
| CN | 105190578 A | 12/2015 |
| CN | 106102504 A | 11/2016 |
| EP | 2198521 B1 | 6/2012 |
| EP | 2959394 A1 | 12/2015 |
| EP | 3104737 A1 | 12/2016 |
| JP | H05-277080 A | 10/1993 |
| JP | 2005-095561 A | 4/2005 |
| JP | 2010-520561 A | 6/2010 |
| JP | 2016-507851 A | 3/2016 |
| JP | 2017-509386 A | 4/2017 |
| KR | 2015-0123254 A | 11/2015 |
| KR | 2016-0121552 A | 10/2016 |
| KR | 10-1790147 B1 | 10/2017 |
| WO | WO 2008/109248 A2 | 9/2008 |
| WO | WO 2009/042313 A1 | 4/2009 |
| WO | WO 2010/104879 A2 | 9/2010 |
| WO | WO 2012/155157 A1 | 11/2012 |
| WO | WO 2014/130871 A1 | 8/2014 |
| WO | WO 2014/186370 A1 | 11/2014 |
| WO | WO 2014/194257 A1 | 12/2014 |
| WO | WO 2014/197443 A1 | 12/2014 |
| WO | WO 2015/027089 A1 | 2/2015 |
| WO | WO 2015/073713 A1 | 5/2015 |
| WO | WO 2015/081113 A1 | 6/2015 |
| WO | WO 2015/123445 A1 | 8/2015 |
| WO | WO 2015/199747 A1 | 12/2015 |
| WO | WO 2016/041088 A1 | 3/2016 |
| WO | WO 2017/062544 A1 | 4/2017 |
| WO | WO 2017/092225 A1 | 6/2017 |
| WO | WO 2017/120669 A1 | 7/2017 |
| WO | WO 2017/172185 A1 | 10/2017 |
| WO | WO 2017/208167 A1 | 12/2017 |

OTHER PUBLICATIONS

Al-Timemy, Ali H., Rami N. Khushaba, Guido Bugmann, and Javier Escudero. "Improving the performance against force variation of EMG controlled multifunctional upper-limb prostheses for transradial amputees." IEEE Transactions on Neural Systems and Rehabilitation Engineering 24, No. 6 (2015): 650-661. (Year: 2015).*

Wolf, Michael T., Christopher Assad, Matthew T. Vernacchia, Joshua Fromm, and Henna L. Jethani. "Gesture-based robot control with variable autonomy from the JPL BioSleeve." In 2013 IEEE International Conference on Robotics and Automation, pp. 1160-1165. IEEE, 2013. (Year: 2013).*

Extended European Search Report for European Application No. EP 17835111.0 dated Nov. 21, 2019.

Extended European Search Report for European Application No. EP 17835140.9 dated Nov. 26, 2019.

International Search Report and Written Opinion for International Application No. PCT/US2019/042579 dated Oct. 31, 2019.

Invitation to Pay Additional Fees for International Application No. PCT/US2019/049094 dated Oct. 24, 2019.

International Search Report and Written Opinion for International Application No. PCT/US2019/052131 dated Dec. 6, 2019.

International Search Report and Written Opinion for International Application No. PCT/US2019/046351 dated Nov. 7, 2019.

Al-Mashhadany, Inverse Kinematics Problem (IKP) of 6-DOF Manipulator Bgy Locally Recurrent Neural Networks (LRNNs). Management and Service Science (MASS). 2010 International Conference on, IEEE. Aug. 24, 2010. 5 pages. ISBN: 978-1-4244-5325-2.

Kipke et al., Silicon-substrate Intracortical Microelectrode Arrays for Long-Term Recording of Neuronal Spike Activity in Cerebral Cortex. IEEE Transactions on Neural Systems and Rehabilitation Engineering. 2003;11(2):151-155.

Marcard et al., Sparse Inertial Poser: Automatic 3D Human Pose Estimation from Sparse IMUs. Eurographics. 2017;36(2). 12 pages.

Wittevrongel et al., Spatiotemporal Beamforming: A Transparent and Unified Decoding Approach to Synchronous Visual Brain-Computer Interfacing. Frontiers in Neuroscience. 2017;11:1-12.

Zacharaki et al., Spike pattern recognition by supervised classification in low dimensional embedding space. Brain Informatics. 2016;3:73-8. DOI: 10.1007/s40708-016-0044-4.

International Search Report and Written Opinion for International Application No. PCT/US2017/043686 dated Oct. 6, 2017.

International Preliminary Report on Patentability for International Application No. PCT/US2017/043686 dated Feb. 7, 2019.

International Search Report and Written Opinion for International Application No. PCT/US2017/043693 dated Oct. 6, 2017.

International Preliminary Report on Patentability for International Application No. PCT/US2017/043693 dated Feb. 7, 2019.

International Search Report and Written Opinion for International Application No. PCT/US2017/043791 dated Oct. 5, 2017.

International Preliminary Report on Patentability for International Application No. PCT/US2017/043791 dated Feb. 7, 2019.

International Search Report and Written Opinion for International Application No. PCT/US2017/043792 dated Oct. 5, 2017.

International Preliminary Report on Patentability for International Application No. PCT/US2017/043792 dated Feb. 7, 2019.

International Search Report and Written Opinion for International Application No. PCT/US2018/056768 dated Jan. 15, 2019.

International Search Report and Written Opinion for International Application No. PCT/US2018/061409 dated Mar. 12, 2019.

International Search Report and Written Opinion for International Application No. PCT/US2018/063215 dated Mar. 21, 2019.

International Search Report and Written Opinion for International Application No. PCT/US2019/015134 dated May 15, 2019.

International Search Report and Written Opinion for International Application No. PCT/US2019/015167 dated May 21, 2019.

International Search Report and Written Opinion for International Application No. PCT/US2019/015174 dated May 21, 2019.

International Search Report and Written Opinion for International Application No. PCT/US2019/015238 dated May 16, 2019.

International Search Report and Written Opinion for International Application No. PCT/US2019/015183 dated May 3, 2019.

International Search Report and Written Opinion for International Application No. PCT/US2019/015180 dated May 28, 2019.

International Search Report and Written Opinion for International Application No. PCT/US2019/015244 dated May 16, 2019.

International Search Report and Written Opinion for International Application No. PCT/US2019/037302 dated Oct. 11, 2019.

International Search Report and Written Opinion for International Application No. PCT/US2019/028299 dated Aug. 9, 2019.

International Search Report and Written Opinion for International Application No. PCT/US2019/034173 dated Sep. 18, 2019.

Invitation to Pay Additional Fees for International Application No. PCT/US2019/031114 dated Aug. 6, 2019.

International Search Report and Written Opinion for International Application No. PCT/US19/20065 dated May 16, 2019.

Arkenbout et al., Robust Hand Motion Tracking through Data Fusion of 5DT Data Glove and Nimble VR Kinect Camera Measurements. Sensors. 2015;15:31644-71.

Benko et al., Enhancing Input on and Above the Interactive Surface with Muscle Sensing. The ACM International Conference on Interactive Tabletops and Surfaces. ITS '09. 2009:93-100.

Boyali et al., Spectral Collaborative Representation based Classification for hand gestures recognition on electromyography signals. Biomedical Signal Processing and Control. 2016;24:11-18.

Cheng et al., A Novel Phonology- and Radical-Coded Chinese Sign Language Recognition Framework Using Accelerometer and Surface Electromyography Sensors. Sensors. 2015;15:23303-24.

Csapo et al., Evaluation of Human-Myo Gesture Control Capabilities in Continuous Search and Select Operations. 7th IEEE International Conference on Cognitive Infocommunications. 2016;000415-20.

Davoodi et al., Development of a Physics-Based Target Shooting Game to Train Amputee Users of Multijoint Upper Limb Prostheses. Presence. Massachusetts Institute of Technology. 2012;21(1):85-95.

(56) References Cited

OTHER PUBLICATIONS

Delis et al., Development of a Myoelectric Controller Based on Knee Angle Estimation. Biodevices 2009. International Conference on Biomedical Electronics and Devices. Jan. 17, 2009. 7 pages.

Diener et al., Direct conversion from facial myoelectric signals to speech using Deep Neural Networks. 2015 International Joint Conference on Neural Networks (IJCNN). Oct. 1, 2015. 7 pages.

Ding et al., HMM with improved feature extraction-based feature parameters for identity recognition of gesture command operators by using a sensed Kinect-data stream. Neurocomputing. 2017;262:108-19.

Farina et al., Man/machine interface based on the discharge timings of spinal motor neurons after targeted muscle reinnervation. Nature. Biomedical Engineering. 2017;1:1-12.

Favorskaya et al., Localization and Recognition of Dynamic Hand Gestures Based on Hierarchy of Manifold Classifiers. International Archives of the Photogrammetry, Remote Sensing and Spatial Information Sciences. 2015;XL-5/W6:1-8.

Gallina et al., Surface EMG Biofeedback. Surface Electromyography: Physiology, Engineering, and Applications. 2016:485-500.

Hauschild et al., A Virtual Reality Environment for Designing and Fitting Neural Prosthetic Limbs. IEEE Transactions on Neural Systems and Rehabilitation Engineering. 2007;15(1):9-15.

Jiang, Purdue University Graduate School Thesis/Dissertation Acceptance. Graduate School Form 30. Updated Jan. 15, 2015. 24 pages.

Kawaguchi et al., Estimation of Finger Joint Angles Based on Electromechanical Sensing of Wrist Shape. IEEE Transactions on Neural Systems and Rehabilitation Engineering. 2017;25(9):1409-18.

Kim et al., Real-Time Human Pose Estimation and Gesture Recognition from Depth Images Using Superpixels and SVM Classifier. Sensors. 2015;15:12410-27.

Koerner, Design and Characterization of the Exo-Skin Haptic Device: A Novel Tendon Actuated Textile Hand Exoskeleton. 2017. 5 pages.

Lee et al., Motion and Force Estimation System of Human Fingers. Journal of Institute of Control, Robotics and Systems. 2011;17(10):1014-1020.

Li et al., Motor Function Evaluation of Hemiplegic Upper-Extremities Using Data Fusion from Wearable Inertial and Surface EMG Sensors. Sensors. MDPI. 2017;17(582):1-17.

Lopes et al., Hand/arm gesture segmentation by motion using IMU and EMG sensing. ScienceDirect. Elsevier. Procedia Manufacturing. 2017;11:107-13.

Martin et al., A Novel Approach of Prosthetic Arm Control using Computer Vision, Biosignals, and Motion Capture. IEEE. 2014. 5 pages.

McIntee, A Task Model of Free-Space Movement-Based Gestures. Dissertation. Graduate Faculty of North Carolina State University. Computer Science. 2016. 129 pages.

Mendes et al., Sensor Fusion and Smart Sensor in Sports and Biomedical Applications. Sensors. 2016;16(1569):1-31.

Mohamed, Homogeneous cognitive based biometrics for static authentication. Dissertation submitted to University of Victoria, Canada. Feb. 1, 2011. 149 pages. URL:http://hdl.handle.net/1828/3211 [last accessed Oct. 11, 2019].

Naik et al., Source Separation and Identification issues in bio signals: A solution using Blind source separation. Intech. 2009. 23 pages.

Naik et al., Subtle Hand gesture identification for HCI using Temporal Decorrelation Source Separation BSS of surface EMG. Digital Image Computing Techniques and Applications. IEEE Computer Society. 2007;30-7.

Negro et al., Multi-channel intramuscular and surface EMG decomposition by convolutive blind source separation. Journal of Neural Engineering. 2016;13:1-17.

Saponas et al., Demonstrating the Feasibility of Using Forearm Electromyography for Muscle-Computer Interfaces. CHI 2008 Proceedings. Physiological Sensing for Input. 2008:515-24.

Saponas et al., Enabling Always-Available Input with Muscle-Computer Interfaces. UIST '09. 2009:167-76.

Saponas et al., Making Muscle-Computer Interfaces More Practical. CHI 2010: Brauns and Brawn. 2010:851-4.

Sartori et al., Neural Data-Driven Musculoskeletal Modeling for Personalized Neurorehabilitation Technologies. IEEE Transactions on Biomedical Engineering. 2016;63(5):879-93.

Sauras-Perez et al., A Voice and Pointing Gesture Interaction System for Supporting Human Spontaneous Decisions in Autonomous Cars. Clemson University. All Dissertations. 2017. 174 pages.

Shen et al., I am a Smartwatch and I can Track my User's Arm. University of Illinois at Urbana-Champaign. MobiSys' 16. 12 pages.

Son et al., Evaluating the utility of two gestural discomfort evaluation methods. PLOS One. 2017. 21 pages.

Strbac et al., Microsoft Kinect-Based Artificial Perception System for Control of Functional Electrical Stimulation Assisted Grasping. Hindawi Publishing Corporation. BioMed Research International. 2014. 13 pages.

Torres, Myo Gesture Control Armband. PCMag. Https://www.pcmag.com/article2/0,2817,2485462,00.asp 2015. 9 pages.

Valero-Cuevas et al., Computational Models for Neuromuscular Function. NIH Public Access Author Manuscript. Jun. 16, 2011. 52 pages.

Wodzinski et al., Sequential Classification of Palm Gestures Based on A* Algorithm and MLP Neural Network for Quadrocopter Control. Metrol. Meas. Syst., 2017;24(2):265-76.

Xue et al., Multiple Sensors Based Hand Motion Recognition Using Adaptive Directed Acyclic Graph. Applied Sciences. MDPI. 2017;7(358):1-14.

Yang et al., Surface EMG based handgrip force predictions using gene expression programming. Neurocomputing. 2016;207:568-579.

* cited by examiner

METHODS AND APPARATUS FOR UNSUPERVISED ONE-SHOT MACHINE LEARNING FOR CLASSIFICATION OF HUMAN GESTURES AND ESTIMATION OF APPLIED FORCES

BACKGROUND

Systems that utilize machine learning techniques to recognize and model gestures performed by a user typically require large sets of labeled data or training samples, which are labeled by humans and susceptible to human bias or labeling errors. For example, in an image recognition context, a supervised learning model is trained to recognize gestures based on labeled data, such as, multiple images capturing different angles for a particular gesture, where the images are labeled by humans to indicate the angles, types, and other aspects of the gesture.

SUMMARY

In a system that recognizes and models human gestures, the inventors have appreciated that it is desirable for the system to rapidly learn gestures from few training samples. It may also be desirable for the system to capture and interpret meaningful features from the gestures in an unsupervised way, for instance, using unlabeled training data. Such meaningful features may include features indicative of a force or amount of force applied during performance of a gesture, which can convey different meaning. For example, different amounts of force applied to a same gesture may allow the system to generate different command signals for controlling objects in virtual or augmented reality environments, controlling devices in a user's environment, or other suitable systems and/or devices.

Some embodiments are directed to an apparatus, comprising a processor, a plurality of neuromuscular sensors coupled to the processor, and a memory storing instructions. The instructions, when executed by the processor, cause the processor to: receive, via the plurality of neuromuscular sensors, a first plurality of neuromuscular signals from a user as the user performs a first single act of a gesture and train a classification model based on the first plurality of neuromuscular signals. Training the classification model comprises: deriving one or more values from the first plurality of neuromuscular signals, the one or more values indicative of distinctive features of the gesture including at least one feature that linearly varies with a force applied during performance of the gesture; and generating a first categorical representation of the gesture in the classification model based on the one or more values derived from the first plurality of neuromuscular signals. The instructions, when executed by the processor, cause the processor to: receive, via the plurality or neuromuscular sensors, a second plurality of neuromuscular signals from the user as the user performs a second single act of the gesture; and determine that the user performed the second single act of the gesture based on the classification model and the second plurality of neuromuscular signals.

Other embodiments are directed to an apparatus, comprising a processor, a plurality of neuromuscular sensors coupled to the processor, and a memory storing instructions. The instructions, when executed by the processor, cause the processor to: train a classification model based on a first plurality of neuromuscular signals and a second plurality of neuromuscular signals, the first plurality of neuromuscular signals and the second plurality of neuromuscular signals received via the plurality of neuromuscular sensors. The training comprises deriving, based on a clustering technique, a first set of values indicative of distinctive features of a first gesture including at least one feature that linearly varies with a force applied during performance of the first gesture and a second set of values indicative of distinctive features of a second gesture including at least one feature that linearly varies with a force applied during performance of the second gesture; and generate a categorical representation of the first gesture and a categorical representation of the second gesture in the classification model. The instructions, when executed by the processor, cause the processor to determine, based at least in part on a third plurality of neuromuscular signals and the classification model, whether a user performed a subsequent act of the first gesture or the second gesture.

Other embodiments are directed to a method comprising receiving, at a processor of a wearable device, a plurality of neuromuscular signals from a plurality of neuromuscular sensors included in the wearable device, the plurality of neuromuscular signals corresponding to neuromuscular signals sampled from a user as the user performs a single act of a gesture; training, via an unsupervised machine learning technique, a classification model based on the single act of the gesture, the classification model comprising a categorical representation of the gesture; determining, based on the categorical representation of the gesture, whether the user has performed a subsequent single act of the gesture; determining at least one force value corresponding to a force applied by the user during performance of the subsequent single act of the gesture; and generating a command signal to be communicated to a device in response to a determination that the user has performed the subsequent single act of the gesture, wherein the command signal is indicative of the gesture and the at least one force value applied during performance of the gesture.

Yet other embodiments are directed to a computerized system for training a classification model based on a single act of a first gesture. The system comprises a plurality of neuromuscular sensors configured to record a plurality of neuromuscular signals from a user as the user performs the single act of the first gesture; and at least one computer processor programmed to: train, using an unsupervised machine learning technique, the classification model to create a unique representation of the gesture in the classification model based on at least some of the plurality of neuromuscular signals.

In one aspect, the at least one computer processor is further programmed to identify at least one activity period within the recorded plurality of neuromuscular signals, wherein the at least some of the plurality of neuromuscular signals used for training the classification model are neuromuscular signals recorded during the at least one activity period.

In another aspect, the at least some of the plurality of neuromuscular signals used for training the classification model do not include neuromuscular signals indicative of rest or neutral positions.

In another aspect, identifying at least one activity period comprises identifying an activity period as a time period during which a power value associated with each of the plurality of neuromuscular signals is above a threshold value.

In another aspect, creating a unique representation of the first gesture in the classification model comprises processing the at least some of the plurality of neuromuscular signals to generate a plurality of points in a component feature space;

and clustering at least some of the generated points to create the unique representation of the first gesture.

In another aspect, processing the at least some of the plurality of neuromuscular signals to generate the plurality of points in a component feature space comprises performing a principal component analysis on the at least some of the plurality of neuromuscular signals.

In another aspect, clustering at least some of the generated points comprises applying a K-means clustering analysis to generate one or more clusters of points in the component feature space; and including the one or more clusters of points in the unique representation of the first gesture based on a similarity metric.

In another aspect, the similarity metric comprises a cosine distance.

In another aspect, creating the unique representation of the first gesture comprises generating a vector in the component feature space based on the generated points.

In another aspect, points along the vector represent performance of the first gesture using different amounts of force.

In another aspect, the at least one computer processor is further programmed to associate a first control signal with the unique representation of the first gesture.

In another aspect, the at least one computer processor is further programmed to associate the first control signal and a second control signal with the unique representation of the first gesture, wherein the system is configured to generate the first control signal when the first gesture is performed while applying a force that is below a threshold value and to generate the second control signal when the first gesture is performed while applying a force that is equal to or above the threshold value.

In another aspect, the plurality of neuromuscular sensors are further configured to record a second plurality of neuromuscular signals as the user performs a single act of a second gesture; and the at least one computer processor programmed to: train, using an unsupervised machine learning technique, the classification model to create a unique representation of the second gesture in the classification model based on at least some of the second plurality of neuromuscular signals.

In another aspect, creating a unique representation of the second gesture in the classification model comprises: processing the at least some of the second plurality of neuromuscular signals to generate a plurality of second points in the component feature space; and clustering at least some of the plurality of second points to create the unique representation of the second gesture.

In another aspect, creating a unique representation of the first gesture in the classification model comprises: processing the at least some of the plurality of neuromuscular signals to generate a first plurality of points in a component feature space; and generating a first vector in the component feature space based on the generated first plurality of points, wherein creating the unique representation of the second gesture comprises generating a second vector in the component feature space based on the second plurality of points, and wherein the second vector associated with the second gesture is different than a first vector associated with the first gesture.

In another aspect, the plurality of neuromuscular sensors are arranged on one or more wearable devices.

Other embodiments are directed to a computerized system for classifying a gesture performed by a user. The system comprises a plurality of neuromuscular sensors configured to record a plurality of neuromuscular signals from the user as the user performs a first gesture; and at least one computer processor. The at least one computer processor is programmed to: create a representation of the first gesture in a component feature space of a classification model, wherein the classification model is trained to include a unique representation of each of a plurality of gestures in the component features space; determine whether the representation of the first gesture corresponds to any of the unique representations of the plurality of gestures included in the classification model; and generate, when it is determined that the representation of the first gesture corresponds to one of the unique representations, a control signal associated with the unique representation.

In one aspect, creating a representation of the first gesture comprises processing the at least some of the plurality of neuromuscular signals to generate a plurality of points in the component feature space; and clustering at least some of the plurality points to create the representation of the first gesture.

In another aspect, processing the at least some of the plurality of neuromuscular signals to generate a plurality of points in the component feature space comprises performing a principal component analysis on the at least some of the plurality of neuromuscular signals.

In another aspect, clustering at least some of the plurality of points comprises: applying a k-means clustering analysis to generate one or more clusters of points in the component feature space; and including the one or more clusters of points in the representation of the first gesture based on a similarity metric.

In another aspect, the similarity metric comprises a cosine distance.

In another aspect, creating the representation of the first gesture comprises generating a first vector in the component feature space based on the plurality of points.

In another aspect, determining whether the representation of the first gesture corresponds to one of the unique representations comprises determining, based on a similarity metric, whether the first vector associated with the first gesture corresponds to one of a plurality of vectors associated with the plurality of gestures.

In another aspect, the similarity metric is a cosine distance between the first vector and each of the plurality of vectors in the component feature space.

In another aspect, the plurality of neuromuscular sensors are arranged on one or more wearable devices.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

FIG. 3A illustrates a wearable portion of the computer-based system and FIG. 3B illustrates a dongle portion connected to a computer, wherein the dongle portion is configured to communicate with the wearable portion;

DETAILED DESCRIPTION

Figure 1:
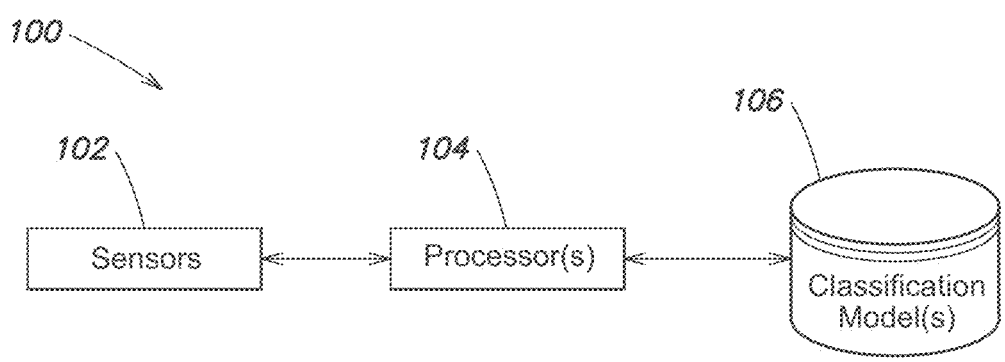
FIG. 1 is a schematic diagram of a computer-based system for processing neuromuscular sensor data in accordance with some embodiments of the technology described herein.

Some existing techniques for recognizing and modeling human gestures use labeled training data that is prone to human errors. Errors in labeling of training data results in inaccurate training of supervised learning models, which in turn, leads to errors in gesture recognition. In addition, such techniques typically require large amounts of labeled training data, which is difficult and time consuming to acquire and produce. Furthermore, processing such large amounts of labeled data consumes significant computing and memory resources.

Some existing techniques for recognizing and modeling human gestures also fail to capture meaningful features associated with the human gestures, such as, a force or amount of force applied during performance of a gesture. For example, in an image recognition context, a supervised learning model may be trained to recognize gestures based on labeled image data. These labeled images reflect a positioning of a person's hand during performance of the gesture, but the labeled images do not reflect information associated with the force that the user applied when performing the gesture.

The inventors have recognized that existing techniques used for recognizing and modeling human gestures may be improved by utilizing an unsupervised machine learning or training approach to train a classification model to recognize and model one or more user-defined gestures and forces applied by users at the time of performing such gestures. The classification model may be trained with unlabeled data obtained from neuromuscular sensors arranged on a wearable device. The unlabeled data may include neuromuscular signals recorded from the neuromuscular sensors.

The inventors have recognized that by utilizing an unsupervised training approach, an example of which, is described in detail below, a classification model can be trained based on neuromuscular signals that are recorded as the user performs a single act of a gesture (also referred to as "one-shot" training or learning). The classification model is trained to recognize the gesture by generating a categorical representation of the gesture in the model. The categorical representation of the gesture may be generated based on one or more features derived from the recorded neuromuscular signals and/or one or more force values associated with a force applied during performance of the gesture. The categorical representation may include a representation via which a type of gesture performed by the user and the amount of force applied by the user during performance of the gesture can be inferred. Using the trained classification model, subsequent performance of the same gesture by the user can be identified based on its categorical representation in the classification model.

According to some embodiments, the classification model can be trained to recognize multiple gestures performed by a user or multiple users. For example, the classification model can be trained based on neuromuscular signals that are recorded as the user performs a single act of each of the gestures. A clustering technique may be utilized to partition the recorded sensor data into a number of clusters, each cluster associated with a particular gesture. A categorical representation of each gesture may be determined based on the associated cluster. For example, the categorical representation may include information identifying the type of gesture, a direction, and a force scale (e.g., a range of force values/amounts) associated with the gesture. After the classification model is trained, the system may determine whether a gesture performed by the user maps to any of the categorical representations associated with the different gestures represented in the classification model.

FIG. 1 illustrates a system 100 in accordance with some embodiments. The system includes a plurality of sensors 102 configured to record signals arising from neuromuscular activity in skeletal muscle of a human body. The term "neuromuscular activity" as used herein refers to neural activation of spinal motor neurons that innervate a muscle, muscle activation, muscle contraction, or any combination of the neural activation, muscle activation, and muscle contraction. Neuromuscular sensors may include one or more electromyography (EMG) sensors, one or more mechanomyography (MMG) sensors, one or more sonomyography (SMG) sensors, a combination of two or more types of EMG sensors, MMG sensors, and SMG sensors, and/or one or more sensors of any suitable type that are configured to detect neuromuscular signals. In some embodiments, the plurality of neuromuscular sensors may be used to sense muscular activity related to a movement of the part of the body controlled by muscles from which the neuromuscular sensors are arranged to sense the muscle activity. Spatial information (e.g., position and/or orientation information) and force information describing the movement may be predicted based on the sensed neuromuscular signals as the user moves over time or performs one or more gestures.

Sensors 102 may include one or more Inertial Measurement Units (IMUs), which measure a combination of physical aspects of motion, using, for example, an accelerometer, a gyroscope, a magnetometer, or any combination of one or more accelerometers, gyroscopes and magnetometers. In some embodiments, IMUs may be used to sense information about the movement of the part of the body on which the IMU is attached and information derived from the sensed data (e.g., position and/or orientation information) may be tracked as the user moves over time. For example, one or more IMUs may be used to track movements of portions of a user's body proximal to the user's torso relative to the sensor (e.g., arms, legs) as the user moves over time or performs one or more gestures.

In embodiments that include at least one IMU and a plurality of neuromuscular sensors, the IMU(s) and neuromuscular sensors may be arranged to detect movement of different parts of the human body. For example, the IMU(s) may be arranged to detect movements of one or more body segments proximal to the torso (e.g., an upper arm), whereas the neuromuscular sensors may be arranged to detect movements of one or more body segments distal to the torso (e.g., a forearm or wrist). It should be appreciated, however, that autonomous sensors may be arranged in any suitable way, and embodiments of the technology described herein are not limited based on the particular sensor arrangement. For example, in some embodiments, at least one IMU and a plurality of neuromuscular sensors may be co-located on a body segment to track movements of body segment using different types of measurements. In one implementation described in more detail below, an IMU sensor and a plurality of EMG sensors are arranged on a wearable device configured to be worn around the lower arm or wrist of a user. In such an arrangement, the IMU sensor may be configured to track movement information (e.g., positioning and/or orientation over time) associated with one or more arm segments, to determine, for example whether the user has raised or lowered their arm, whereas the EMG sensors may be configured to determine movement information associated with wrist or hand segments to determine, for example, whether the user has an open or closed hand configuration.

Each of the sensors 102 includes one or more sensing components configured to sense information about a user. In the case of IMUs, the sensing components may include one or more accelerometers, gyroscopes, magnetometers, or any combination thereof to measure characteristics of body motion, examples of which include, but are not limited to, acceleration, angular velocity, and sensed magnetic field around the body. In the case of neuromuscular sensors, the sensing components may include, but are not limited to, electrodes configured to detect electric potentials on the surface of the body (e.g., for EMG sensors) vibration sensors configured to measure skin surface vibrations (e.g., for MMG sensors), and acoustic sensing components configured to measure ultrasound signals (e.g., for SMG sensors) arising from muscle activity.

In some embodiments, at least some of the plurality of sensors 102 are arranged as a portion of a wearable device configured to be worn on or around part of a user's body. For example, in one non-limiting example, an IMU sensor and a plurality of neuromuscular sensors are arranged circumferentially around an adjustable and/or elastic band such as a wristband or armband configured to be worn around a user's wrist or arm. Alternatively, at least some of the autonomous sensors may be arranged on a wearable patch configured to be affixed to a portion of the user's body. In some embodiments, multiple wearable devices, each having one or more IMUs and/or neuromuscular sensors included thereon may be used to predict musculoskeletal position information for movements that involve multiple parts of the body.

In some embodiments, sensors 102 only include a plurality of neuromuscular sensors (e.g., EMG sensors). In other embodiments, sensors 102 include a plurality of neuromuscular sensors and at least one "auxiliary" sensor configured to continuously record a plurality of auxiliary signals. Examples of auxiliary sensors include, but are not limited to, other autonomous sensors such as IMU sensors, and non-autonomous sensors such as an imaging device (e.g., a camera), a radiation-based sensor for use with a radiation-generation device (e.g., a laser-scanning device), or other types of sensors such as a heart-rate monitor.

In some embodiments, the output of one or more of the sensing components may be processed using hardware signal processing circuitry (e.g., to perform amplification, filtering, and/or rectification). In other embodiments, at least some signal processing of the output of the sensing components may be performed in software. Thus, signal processing of signals recorded by the sensors may be performed in hardware, software, or by any suitable combination of hardware and software, as aspects of the technology described herein are not limited in this respect.

In some embodiments, the recorded sensor data may be processed to compute additional derived measurements or features that are then provided as input to a classification model, as described in more detail below. For example, recorded signals from an IMU sensor may be processed to derive an orientation signal that specifies the orientation of a rigid body segment over time. Sensors 102 may implement signal processing using components integrated with the sensing components, or at least a portion of the signal processing may be performed by one or more components in communication with, but not directly integrated with the sensing components of the sensors.

System 100 also includes one or more computer processors 104 programmed to communicate with sensors 102. For example, signals recorded by one or more of the sensors may be provided to the processor(s), which may be programmed to process signals output by the sensors 102 to train one or more classification models 106, and the trained (or retrained) classification model(s) 106 may be stored for later use in identifying/classifying gestures and generating control/command signals, as described in more detail below. In some embodiments, the processors 104 may be programmed to derive one or more features associated with one or more gestures performed by a user and the derived feature(s) may be used to train the one or more classification models 106. The processors 104 may be programmed to identify a subsequently performed gesture based on the trained one or more classification models 106. In some implementations, the processors 104 may be programmed to utilize the classification model, at least in part, to map an identified gesture to one or more control/command signals.

Figure 2A:
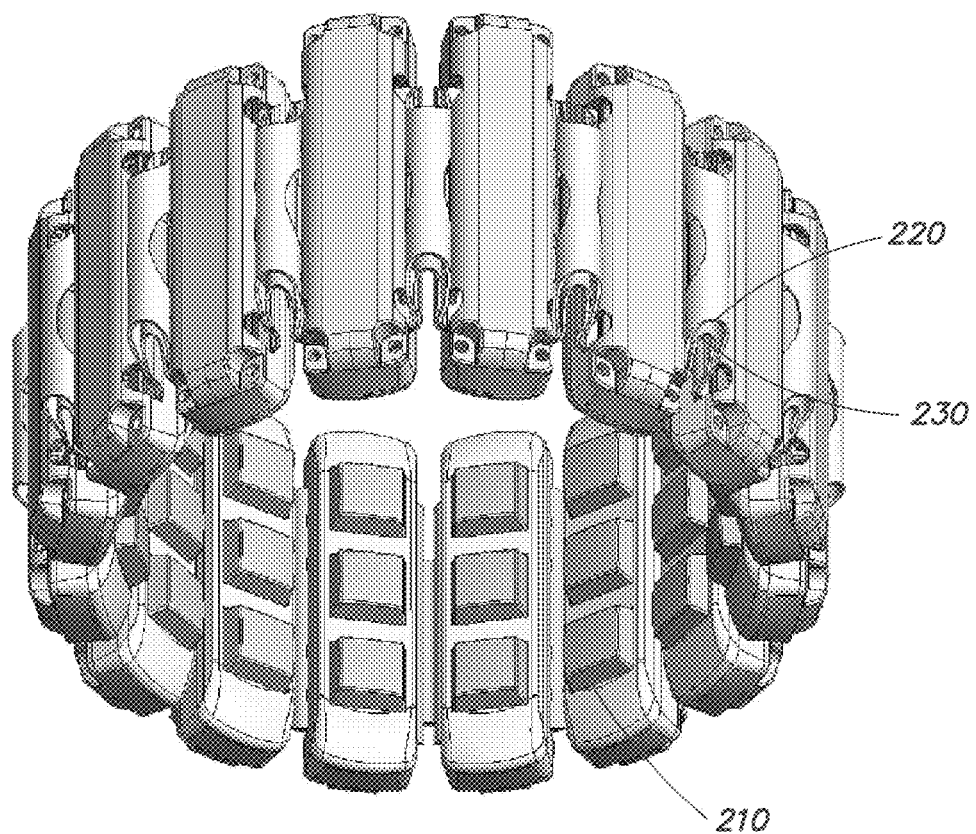
FIG. 2A illustrates a wearable system with sixteen EMG sensors arranged circumferentially around an elastic band configured to be worn around a user's lower arm or wrist, in accordance with some embodiments of the technology described herein.
Figure 2B:
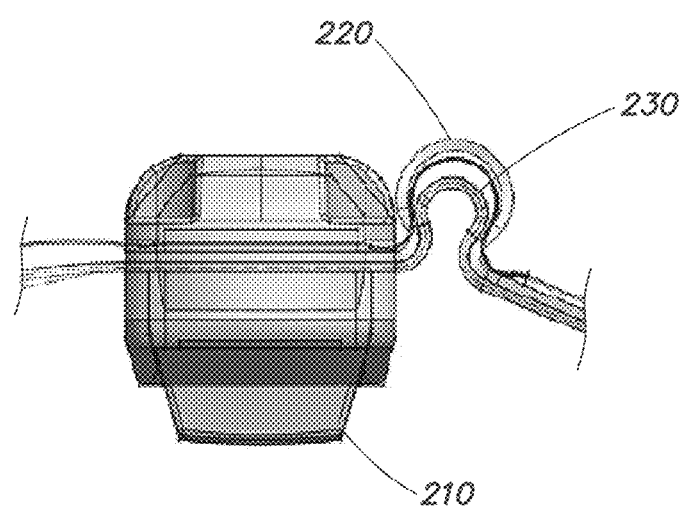
FIG. 2B is a cross-sectional view through one of the sixteen EMG sensors illustrated in FIG. 2A.

FIG. 2A illustrates a wearable system with sixteen neuromuscular sensors 210 (e.g., EMG sensors) arranged circumferentially around an elastic band 220 configured to be worn around a user's lower arm or wrist. As shown, EMG sensors 210 are arranged circumferentially around elastic band 220. It should be appreciated that any suitable number of neuromuscular sensors may be used. The number and arrangement of neuromuscular sensors may depend on the particular application for which the wearable device is used. For example, a wearable armband or wristband can be used to generate control information for controlling an augmented reality system, a virtual reality system, a robot, controlling a vehicle, scrolling through text, controlling a virtual avatar, or any other suitable control task. As shown the sensors 210 may be coupled together using flexible electronics 230 incorporated into the wearable device. FIG. 2B illustrates a cross-sectional view through one of the sensors 210 of the wearable device shown in FIG. 2A.

In some embodiments, the output of one or more of the sensors can be optionally processed using hardware signal processing circuitry (e.g., to perform amplification, filtering, and/or rectification). In other embodiments, at least some signal processing of the output of the sensors can be performed in software. Thus, processing of signals sampled by the sensors can be performed in hardware, software, or by any suitable combination of hardware and software, as aspects of the technology described herein are not limited in this respect. A non-limiting example of a signal processing chain used to process recorded data from sensors 210 is discussed in more detail below in connection with FIGS. 3A and 3B.

Figure 3A:
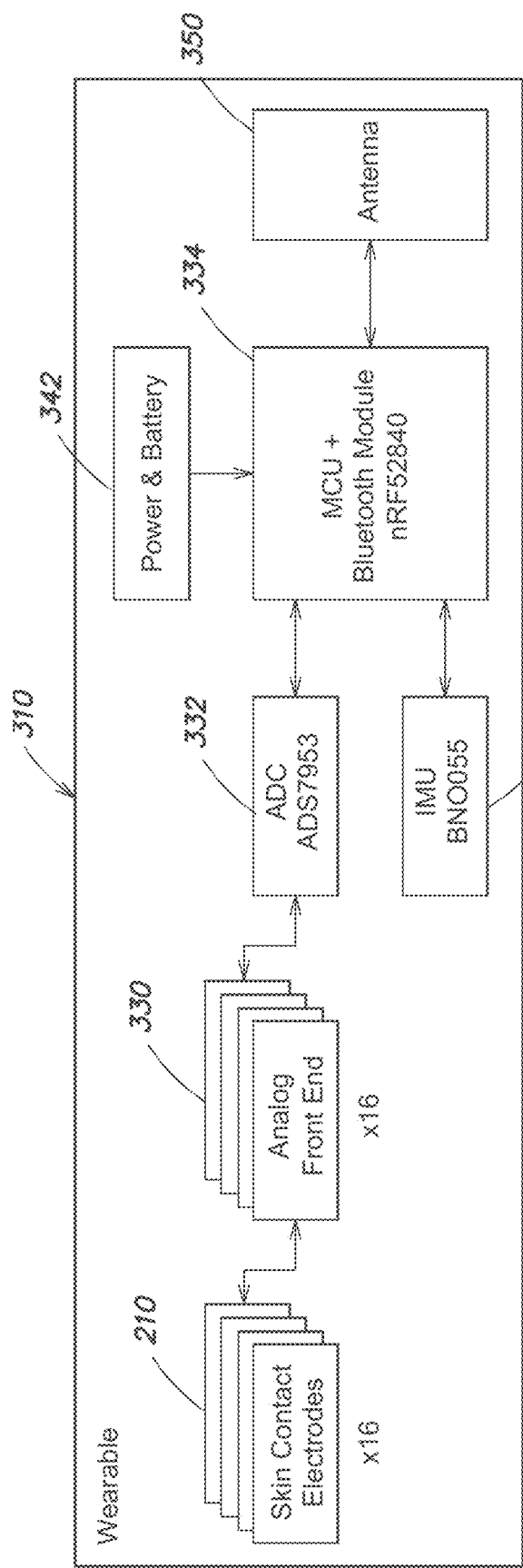
FIGS. 3A and 3B schematically illustrate components of a computer-based system on which some embodiments are implemented.
Figure 3B:
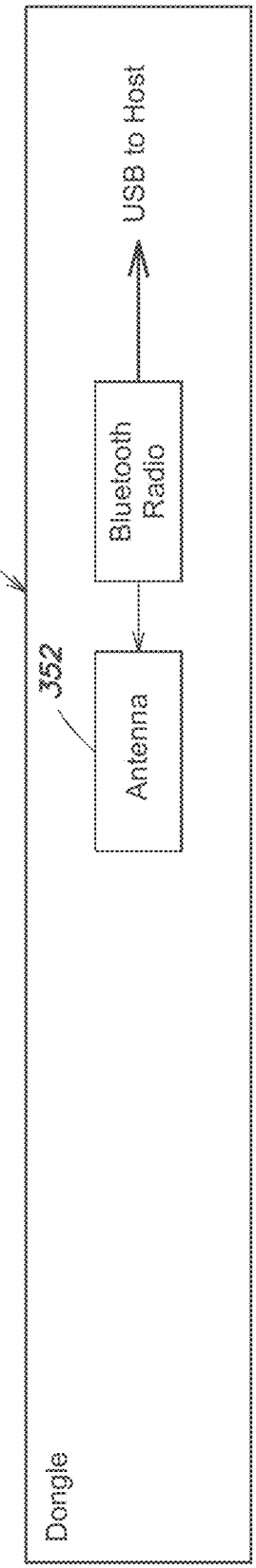

FIGS. 3A and 3B illustrate a schematic diagram showing some internal components of a wearable system with sixteen EMG sensors, in accordance with some embodiments of the technology described herein. As shown, the wearable system includes a wearable portion 310 (FIG. 3A) and a dongle portion 320 (FIG. 3B) in communication with the wearable portion 310 (e.g., via Bluetooth or another suitable short range wireless communication technology). As shown in FIG. 3A, the wearable portion 310 includes the sensors 210, examples of which are described in connection with FIGS. 2A and 2B. The output of the sensors 210 is provided to analog front end 330 configured to perform analog processing (e.g., noise reduction, filtering, etc.) on the recorded signals. The processed analog signals are then provided to analog-to-digital converter 332, which converts the analog signals to digital signals that can be processed by one or more computer processors (e.g., processor 104). An example of a computer processor that may be used in accordance with some embodiments is microcontroller (MCU) 334 illustrated in FIG. 3A. As shown, MCU 334 may also include inputs from other sensors (e.g., IMU sensor 340), and power and battery module 342. The output of the processing performed by MCU may be provided to antenna 350 for transmission to dongle portion 320 shown in FIG. 3B.

Dongle portion 320 includes antenna 352 configured to communicate with antenna 350 included as part of wearable portion 310. Communication between antenna 350 and 352 may occur using any suitable wireless technology and protocol, non-limiting examples of which include radiofrequency signaling and Bluetooth. As shown, the signals received by antenna 352 of dongle portion 320 may be provided to a host computer for further processing, display, and/or for effecting control of a particular physical or virtual object or objects.

Figure 4:
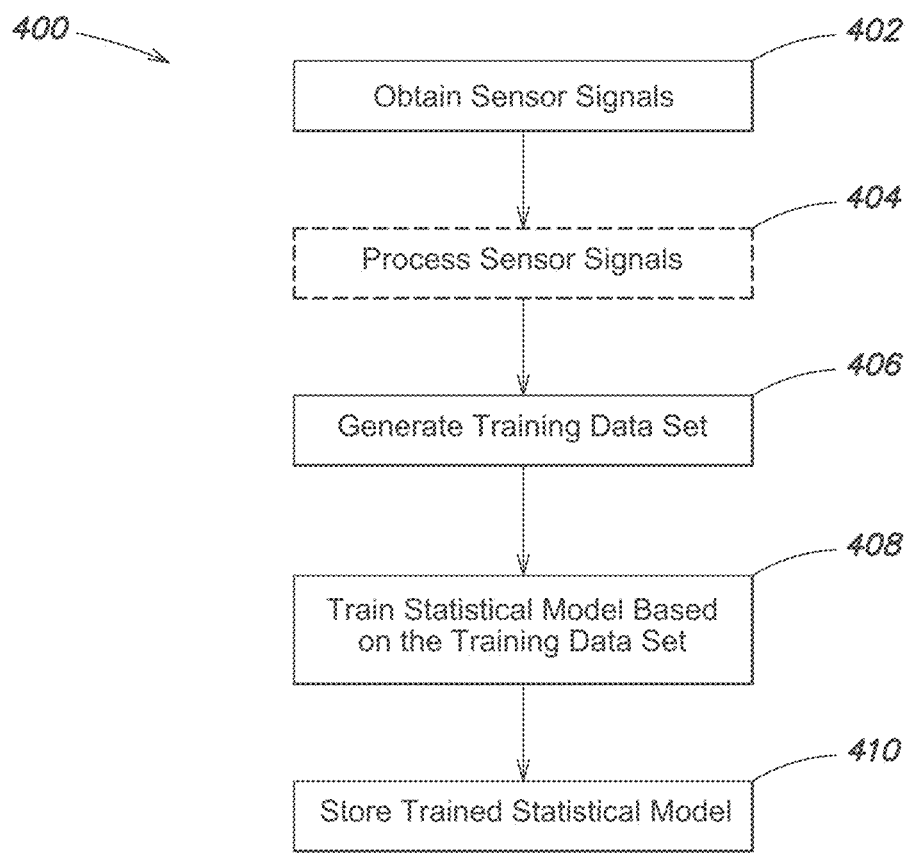
FIG. 4 is a flowchart of a process for generating a classification model based on neuromuscular signals recorded from sensors, in accordance with some embodiments of the technology described herein.

FIG. 4 describes a process 400 for generating (also referred to herein as "training") a classification model 106 using signals recorded from sensors 102 including, for example, sensors 210. FIG. 4 represents a "training phase" for training the classification model. Process 400 may be executed by any suitable computing device(s), as aspects of the technology described herein are not limited in this respect. For example, process 400 may be executed by one or more computer processors described with reference to FIGS. 1, 3A and 3B. As another example, one or more acts of process 400 may be executed using one or more servers (e.g., servers included as a part of a cloud computing environment). For example, at least a portion of act 408 relating to training of a classification model may be performed using a cloud computing environment. In some implementations, the classification model may trained in near real-time. As used herein the term "near real-time" refers to instantaneous perception by the user, e.g., on the order of milliseconds.

Figure 5:
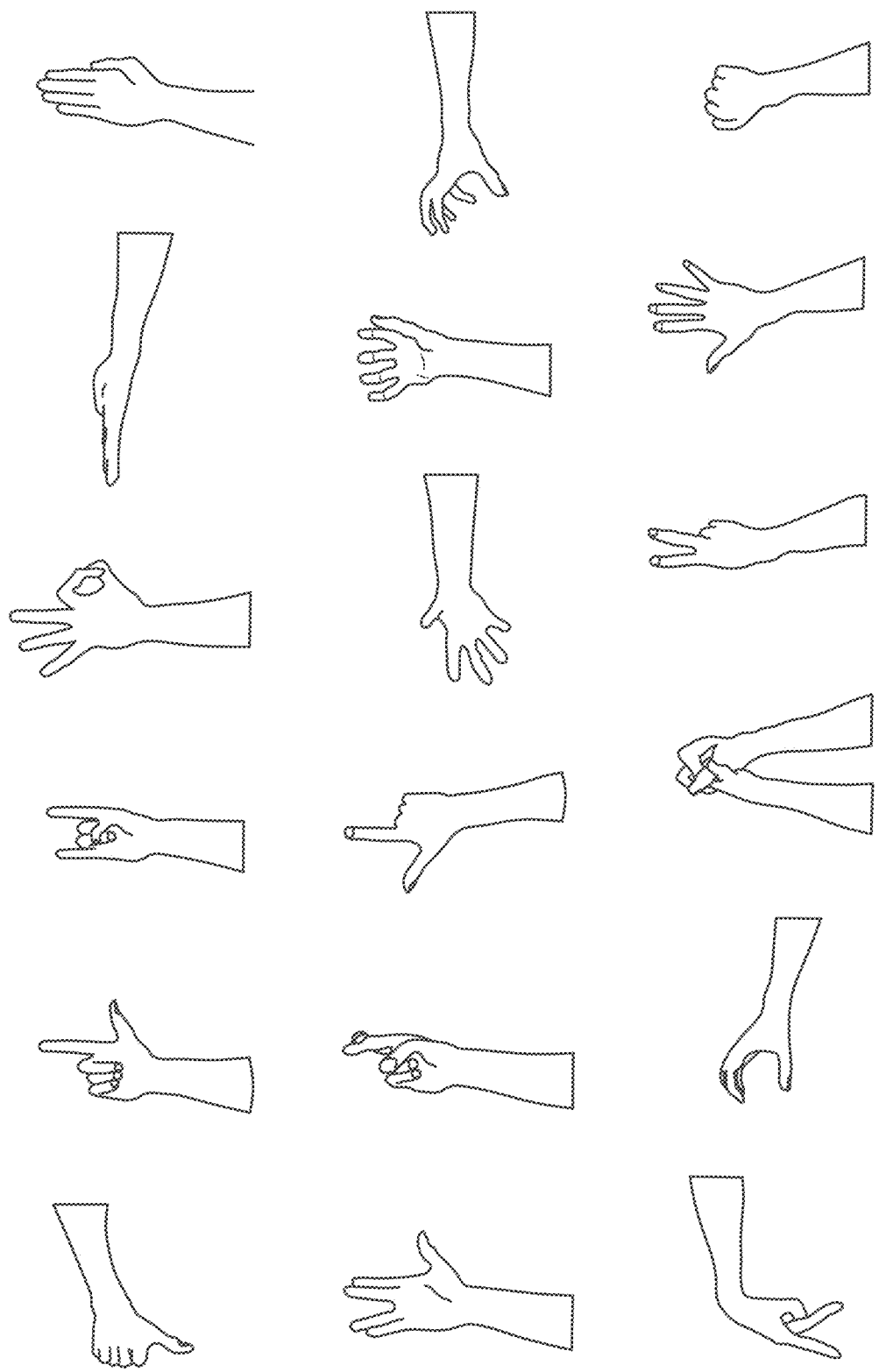
FIG. 5 illustrates examples of user-defined gestures, in accordance with some embodiments of the technology described herein.

Process 400 begins at act 402, where a plurality of sensor signals is obtained for one or multiple users performing one or more gestures, such as gestures depicted in FIG. 5. In some embodiments, the plurality of sensor signals may be recorded as part of process 400. In other embodiments, the plurality of sensor signals may have been recorded prior to the performance of process 400 and are accessed (rather than recorded) at act 402.

As used herein, the term "gestures" refers to a static or dynamic configuration of one or more body parts including the position of the one or more body parts and forces associated with the configuration. For example, gestures include discrete gestures, such as pressing the palm of a hand down on a solid surface or grasping a ball, continuous gestures, such as a waving a finger back and forth or throwing a ball, or a combination of discrete and continuous gestures such as grasping and throwing a ball. Gestures may be arbitrarily defined by a user. In some cases, hand and arm gestures may be symbolic and used to communicate according to cultural standards.

In some embodiments, the gestures may include non-restrictive or customized gestures (also referred to herein as "user-defined" gestures) defined by a user that may represent the user's own and unique collection of gestures. These gestures may not be pre-defined or pre-modeled in the system and the classification model may be trained to identify any type of gesture while applying any amount of force. It will be appreciated that the disclosure is not limited to utilizing or recognizing the gestures depicted in FIG. 5, and any type of user-defined gesture may be utilized.

In some embodiments, the plurality of sensor signals may include sensor signals recorded for a single user performing a single gesture or multiple gestures and the classification model may be trained to recognize the gesture(s) performed by the user. Sensor signals may be recorded as the user performs the gesture(s). The sensor signals may be recorded by any suitable number of sensors located in any suitable location(s) to detect the user's movements indicative of the gesture(s). For example, when the user uses the fingers of his/her right hand to perform a gesture, the sensor signals may be recorded by multiple neuromuscular sensors circumferentially (or otherwise) arranged around the user's lower right arm to detect muscle activity in the lower right arm that give rise to the movements of the user's right hand. One or more IMU sensors may be arranged to predict the joint angle of the user's arm relative to the user's torso. As another example, when the user uses his legs to perform a gesture, sensor signals may be recorded by multiple neuromuscular sensors circumferentially (or otherwise) arranged around the user's leg to detect muscle activity in the leg that give rise to the movements of the foot and one or more IMU sensors may be arranged to predict the joint angle of the user's leg relative to the user's torso.

Figure 6A:
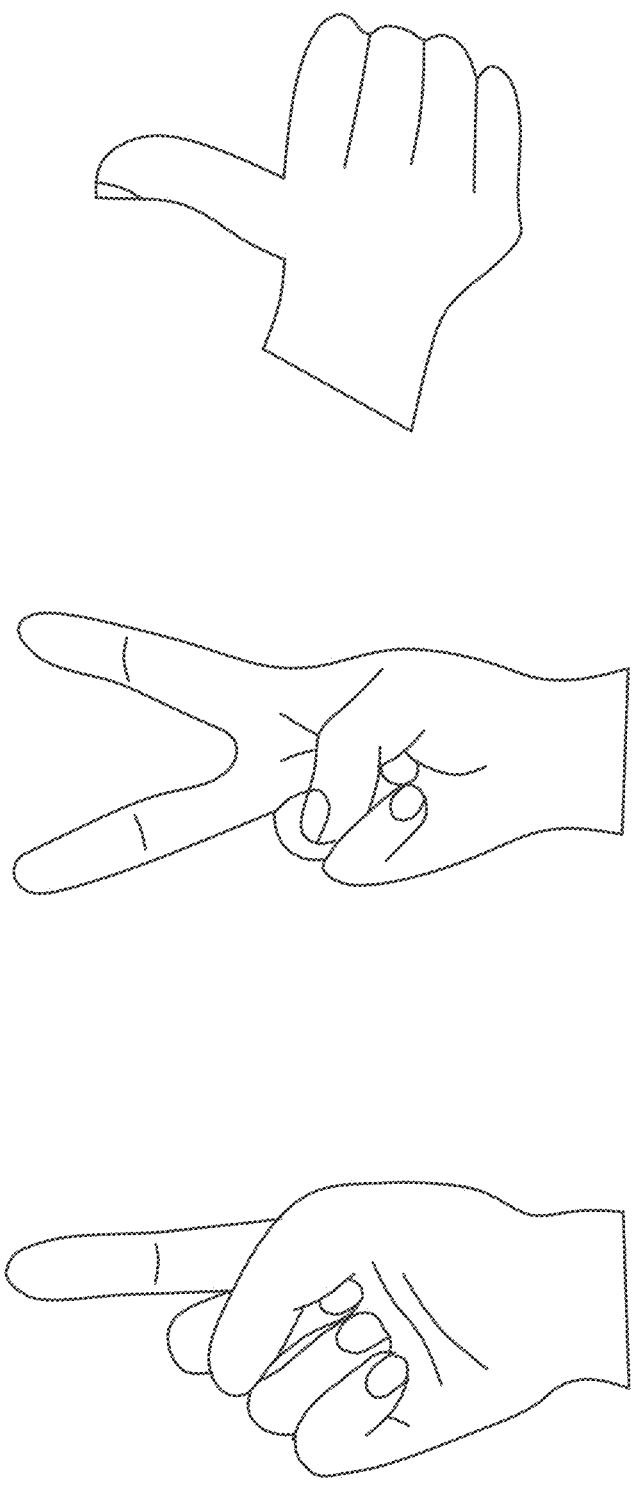
FIG. 6A illustrates a first set of gestures associated with a first user, in accordance with some embodiments of the technology described herein.
Figure 6B:
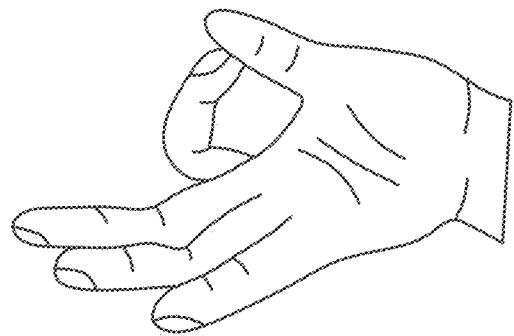
FIG. 6B illustrates a second set of gestures associated with a second user, in accordance with some embodiments of the technology described herein.
Figure 6B:
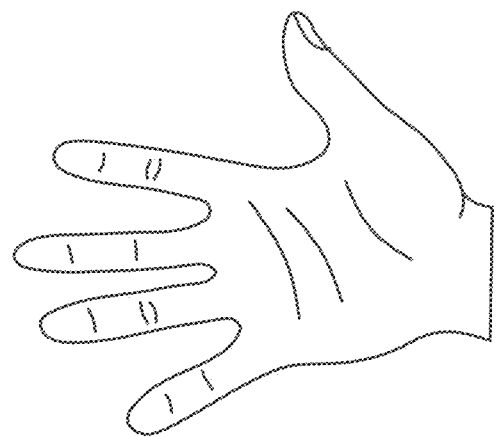
Figure 6B:
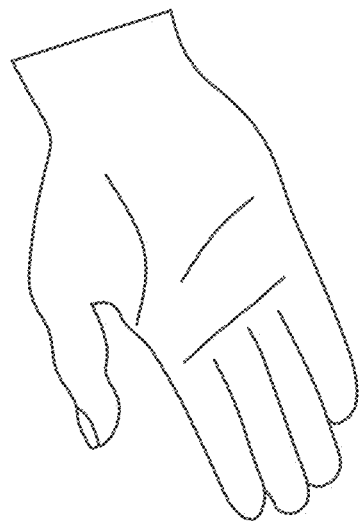

In some embodiments, the plurality of sensor signals may include sensor signals recorded for multiple users performing various gesture(s) and the classification model may be trained to recognize gesture(s) performed by the multiple users. For example, the classification model may be trained to recognize a first set of gestures (shown in FIG. 6A) associated with a first user of the system and a second set of gestures (shown in FIG. 6B) associated with a second user of the system. In some instances, the first set of gestures may be different than the second set of gestures. In some other instances, the first and second set of gestures may be the same. In yet other instances, some gestures in the first set and the second set can overlap (e.g., the sets can have one or more gestures in common).

In some embodiments, the sensor signals obtained in act 402 correspond to signals from one type of sensor (e.g., one or more IMU sensors or one or more neuromuscular sensors) and a classification model may be trained based on the sensor signals recorded using the particular type of sensor, resulting in a sensor-type specific trained classification model. For example, the obtained sensor signals may comprise a plurality of EMG sensor signals arranged around the lower arm or wrist of a user and the classification model may be trained to recognize hand gestures performed by the user(s).

In embodiments that recognize gestures based on multiple types of sensors (e.g., IMU sensors, EMG sensors, MMG sensors, SMG sensors), a separate classification model may be trained for each of the types of sensors and the outputs of the sensor-type specific models may be combined to recognize gesture(s) performed by the user(s). In other embodiments, the sensor signals obtained in act 402 from two or more different types of sensors may be provided to a single classification model that is trained based on the signals recorded from the different types of sensors. In one illustrative implementation, an IMU sensor and a plurality of EMG sensors are arranged on a wearable device configured to be worn around the forearm of a user, and signals recorded by the IMU and EMG sensors are collectively provided as inputs to a classification model, as discussed in more detail below.

In some embodiments, the sensor signals obtained in act 402 are recorded at multiple time points as a user performs one or multiple gestures. As a result, the recorded signal for each sensor may include data obtained at each of multiple time points. Assuming that n sensors are arranged to simultaneously measure the user's movement information during performance of a gesture, the recorded sensor signals for the user may comprise a time series of K n-dimensional vectors $\{x_k | 1 \leq k \leq K\}$ at time points $t_1, t_2, \ldots, t_K$ during performance of the movements.

Next, process 400 proceeds to act 404, where the sensor signals obtained in act 202 are optionally processed. For example, the sensor signals may be processed using amplification, filtering, rectification, or other types of signal processing. In some embodiments, the sensor signals obtained in act 402 may be filtered using a bandpass or high pass filter.

Next, process 400 proceeds to act 406, where a training data set is generated for purposes of training a classification model. The training data set may be generated based on the sensor signals obtained in act 402 or processed sensor signals from act 404. In some embodiments, generating the training data set may include removing certain samples corresponding to rest or neutral positions from the training data set, as described in more detail below.

Next, process 400 proceeds to act 408, where the classification model is trained based on the training data set. In some embodiments, training the classification model may include determining one or more distinctive features associated with the gesture(s) based on values sampled or otherwise derived from the sensor signals (e.g., data obtained at multiple time points) in the training data set. The one or more distinctive features may include a feature that linearly varies with a force applied by the user during performance of the gesture(s) or other properties associated with the gesture (e.g., gesture type, direction, force scale, etc.). According to some aspects, training the classification model may include generating a categorical representation of each of the gestures performed by the user in the classification model. The categorical representation may be generated based on the values derived from the sensor signals that are indicative of the one or more distinctive features.

In some implementations, training the classification model may proceed by providing as input to the model a sequence of data sets each of the data sets in the sequence comprising an n-dimensional vector of sensor data. The classification model may provide as output a likelihood that a particular gesture that the classification model recognized based on the input signals corresponds to the gesture the user performed. For example, the classification model may take as input a sequence of vectors $\{x_k | 1 \leq k \leq K\}$ generated using measurements obtained at time points $t_1, t_2, \ldots, t_K$, where the ith component of vector $x_j$ is a value measured by the ith sensor at time $t_j$ and/or derived from the value measured by the ith sensor at time $t_3$. In another non-limiting example, a derived value provided as input to the classification model may comprise or otherwise be indicative of features extracted from the data from all or a subset of the sensors at and/or prior to time $t_j$ (e.g., a covariance matrix, a cospectral matrix, a power spectrum, a combination thereof, or any other suitable derived representation). Based on such input, the classification model may be trained to recognize gesture (s) performed by a user or multiple users.

In embodiments comprising sensors of different types (e.g., IMU sensors and neuromuscular sensors) configured to simultaneously record different types of movement information during performance of a task, the sensor data for the different types of sensors may be recorded using the same or different sampling rates. When the sensor data is recorded at different sampling rates, at least some of the sensor data may be resampled (e.g., up-sampled or down-sampled) such that all sensor data provided as input to the classification model corresponds to time series data at the same time resolution. Resampling at least some of the sensor data may be performed in any suitable way including, but not limited to using interpolation for upsampling and using decimation for downsampling.

In addition to or as an alternative to resampling at least some of the sensor data when recorded at different sampling rates, some embodiments employ a classification model configured to accept multiple inputs asynchronously. For example, the classification model may be configured to model the distribution of the "missing" values in the input data having a lower sampling rate. Alternatively, the timing of training of the classification model occur asynchronously as input from multiple sensor data measurements becomes available as training data.

Next, process 400 proceeds to act 410, where the trained classification model is stored (e.g., in a datastore—not shown). The trained statistical model may be stored using any suitable format, as aspects of the technology described herein are not limited in this respect. Thus, the classification model generated during execution of process 400 may be used at a later time, for example, to recognize gestures performed by a user or multiple users based on a given set of input sensor data, as described below.

Figure 7:
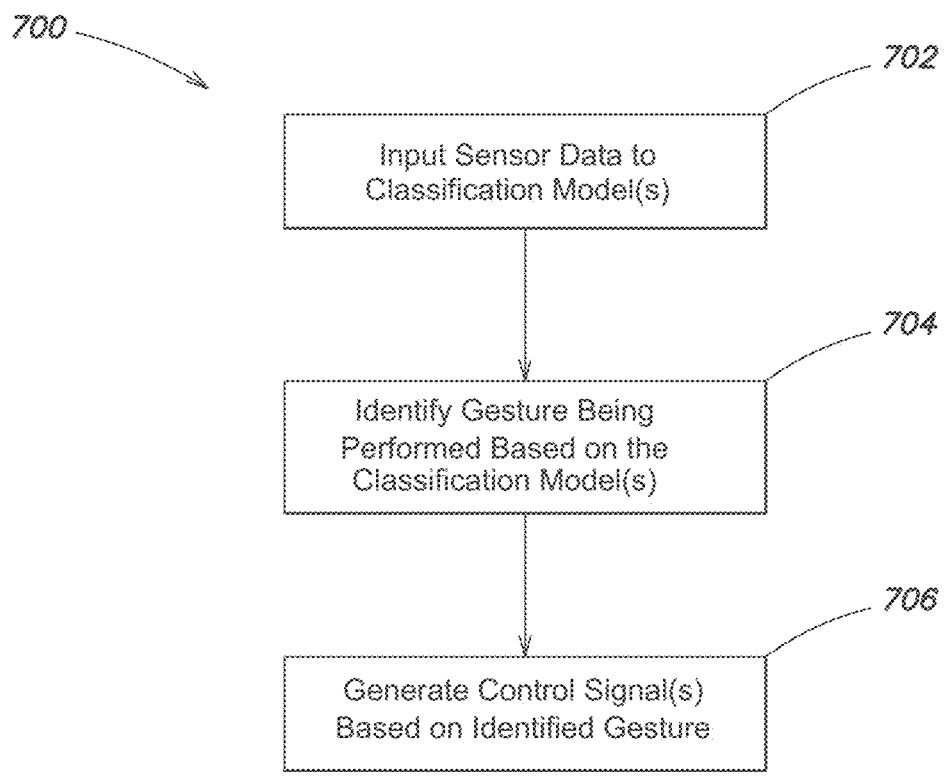
FIG. 7 is a flowchart of a process for identifying gestures based on a trained classification model in accordance with some embodiments of the technology described herein.

FIG. 7 illustrates a process 700 for recognizing user-defined gestures based on recorded sensor data in accordance with some embodiments. FIG. 7 represents a "gesture recognition phase" where the trained classification model is used to recognize gestures being performed by users and generate corresponding command/control signals. In act 702, sensor data recorded by one or more sensors is provided as input to one or more trained classification models that include one or more categorical representations for each of the gestures previously performed by a user or multiple users, as described briefly above.

Process 700 then proceeds to act 704, where the gesture being performed by the user is recognized or identified based on the trained classification model(s). In some embodiments, a determination may be made regarding whether the gesture performed by the user maps to a previously learned gesture in the trained classification model(s). In some embodiments, the neuromuscular signals are recorded continuously during user movements including during performance of the gesture and are provided continuously as input to the trained classification model, resulting in near real-time prediction/recognition of the gesture being performed by the user based on the trained classification model(s).

Process 700 then proceeds to act 706, where one or more command/control signals may be generated based on the identified gesture. The one or more control signals may include signal(s) that activate/deactivate compute devices, control objects in virtual environments, control objects in augmented reality environments, control IoT (Internet of Things) devices, and/or other suitable systems and/or devices. In some embodiments, a single gesture may be configured to generate different signals based on a force a user applies during performance of the gesture. In some embodiments, a level or amount of force applied by the user during performance of the gesture may be determined, for example, in act 704. The measured force may be computed as a continuous variable, ordinal variable, interval variable, descriptive statistic metric or other suitable form.

Example Technique for Training Classification Model(s)—Training Phase

In some implementations, a user wearing the wearable system (depicted in FIGS. 2A, 3A, for example) may consecutively perform a set of gestures (e.g., G1, G2, and G3) or any other number of gestures including just one gesture. The user may perform each of the gestures only once (i.e., perform a single act of each gesture). The system may record and store neuromuscular signals (e.g., EMG signals) as the user performs the gestures. The gestures in the set of gestures can include, for example, G1=first gesture, G2=open hand gesture, and G3=index pinch gesture. As discussed above, other types of gestures different from G1, G2, and G3 can alternatively be performed by a user. In other words, the user is not constrained to performing a pre-defined set of gestures. Rather, an unsupervised machine learning technique used in accordance with some embodiments may be configured to identify any type of gesture (e.g., arm or hand gestures) irrespective of their form.

Figure 8:
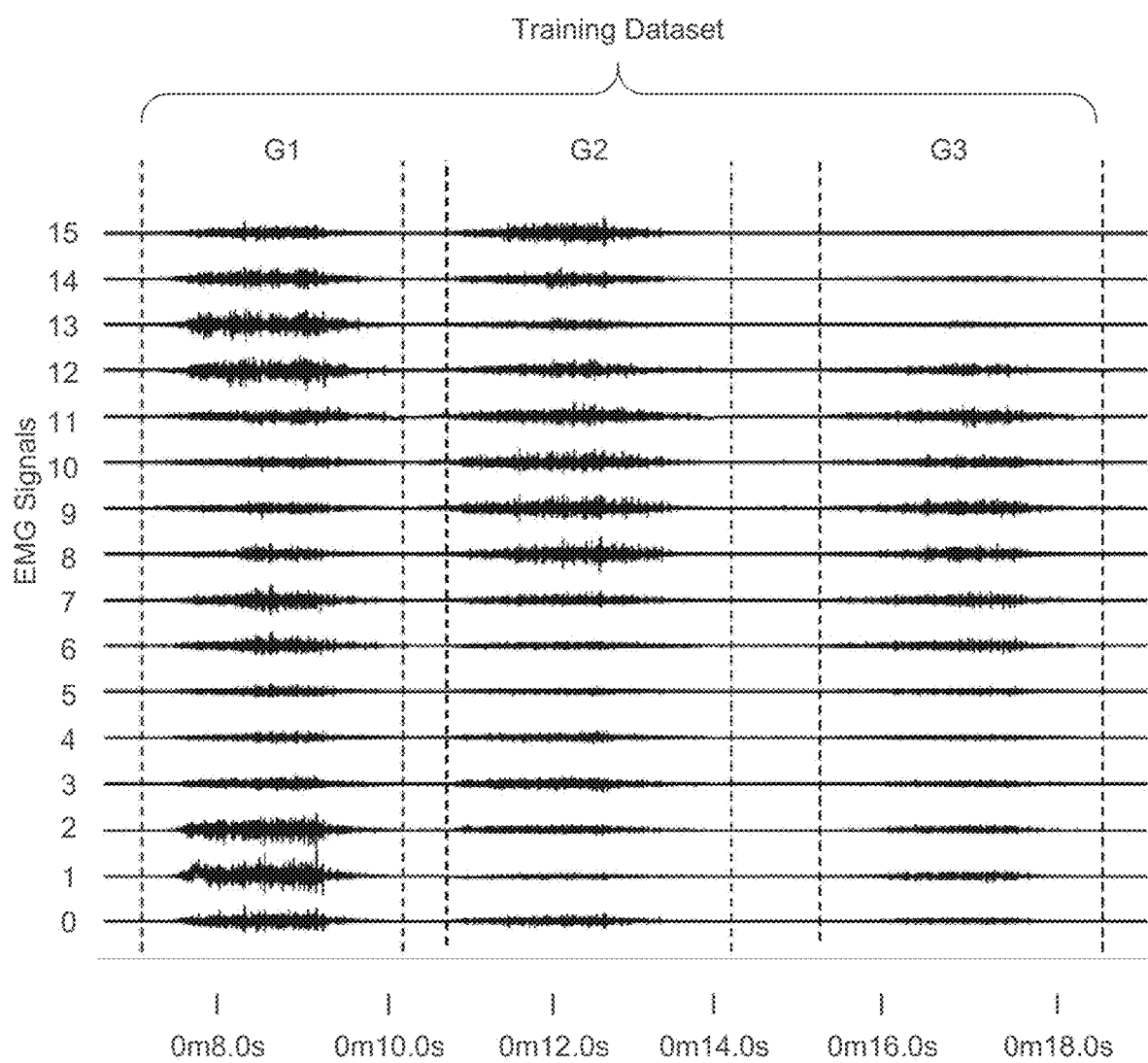
FIG. 8 illustrates signals representing three different gestures captured via sixteen sensors arranged on the wearable system of FIG. 2A, in accordance with some embodiments of the technology described herein.

The system may capture and record a set of neuromuscular signals sampled from the user as the user performs gestures G1, G2, and G3 as shown in FIG. 8. The set of neuromuscular signals may be used as the training data set for the classification model(s). In some embodiments, the set of neuromuscular signals may include signals recorded for each of the sixteen neuromuscular sensors of the wearable system. Each signal in the set may be filtered using, for example, a bandpass, or high pass, or other filtering technique.

In some embodiments, one or more values indicative of distinctive features of each of the gestures may be derived from the set of neuromuscular signals. The distinctive features may include at least one feature that linearly varies with a force applied by the user during performance of the gesture(s). Examples of distinctive features include, but are not limited to, a covariance matrix computed from values sampled from the neuromuscular signals, cospectral matrices computed from the values, a set of filter bank covariance matrices corresponding to different frequencies, and a power spectrum per sensor (e.g., log-PSD (Power Spectral Density) detected by the sensor).

In some implementations, covariances between the filtered signals from EMG sensors (corresponding to sixteen EMG channels) are computed, for example, on a 200 ms window with a stride of 25 ms. Given signal $x(t)$ for the N channels at the time t, the matrix $X=[x(t), \ldots x(t+T)]$ (e.g., a $^N$_channels×T_time_sample matrix) may be defined. Given the centered signal $x(t)$ (e.g., with zero mean after applying a bandpass filter), the covariance matrix can be expressed as:

$$C = XX^T$$

Figure 9:
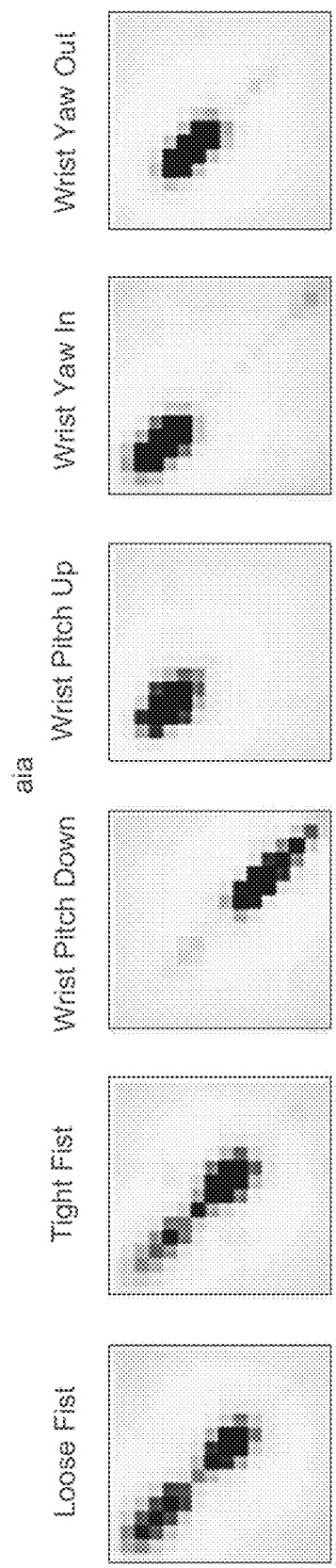
FIG. 9 illustrates examples of covariance matrices computed from neuromuscular signals associated with different gestures, in accordance with some embodiments of the technology described herein.

FIG. 9 illustrates examples of covariance matrices computed for different gestures. The covariance matrix corresponding to the same gesture such as a first may also provide force features and thus the system may be able to differentiate between a loose first gesture (e.g., a first gesture performed with a small amount of force) and a tight first gesture (e.g., a first gesture performed with a large amount of force).

Figure 10:
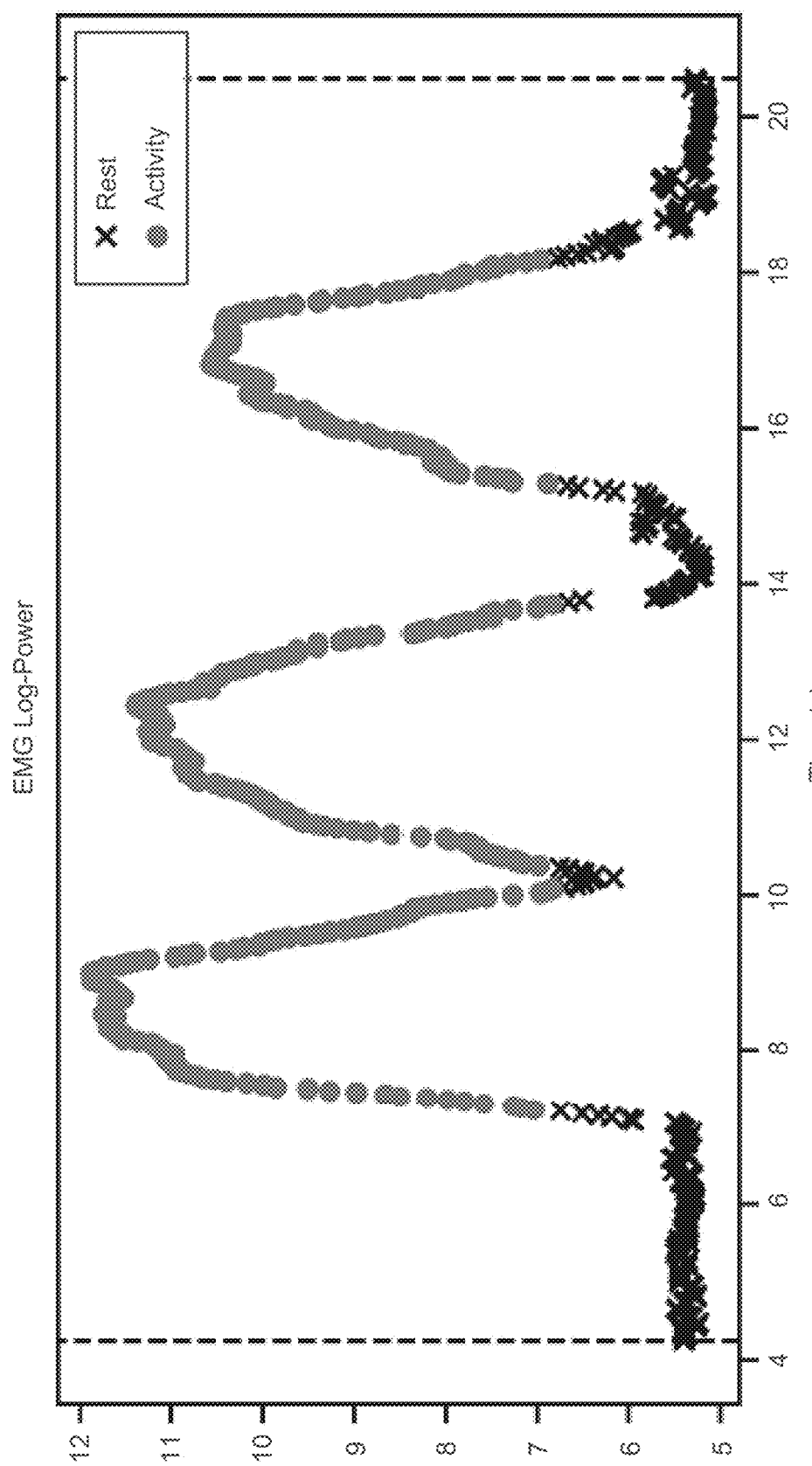
FIG. 10 illustrates a graph showing power values associated with data points corresponding to rest and activity positions, in accordance with some embodiments of the technology described herein.

In some embodiments, samples indicating rest or neutral positions are removed from the training set because such signals are unlikely to include features that can serve to predict or identify a gesture. For example, EMG samples indicating rest or neutral positions can be identified by computing a threshold value (e.g., based on EMG Log-power) that differentiates rest or neutral positions from gesture positions (also referred to herein as activity positions). Accordingly, samples with an EMG Log-power below the computed threshold value may be excluded from the training set. Excluding samples from the training data set (e.g., based on their EMG Log-power) increases the system prediction accuracy and, in some instances, can prevent the system from producing false-positives. For example, in some instances, gestures performed with a negligible amount of force (e.g., below the computed threshold value) can be considered to be executed by the user unintentionally or by accident and as such should not be identified by the system as an intentional gesture. FIG. 10 shows a graph depicting EMG Log-power for data points corresponding to rest and activity positions.

In one embodiment, the threshold value can be computed, for example, by: (a) computing the 10th percentile of the data, and using the computed value as a threshold to capture the data containing activity positions (approximately $90^{th}$ percentile) and containing rest positions (approximately $10^{th}$ percentile), (b) rescaling the samples (e.g., EMG samples) to be between [0,1], then setting the threshold to be 0.1, or (c) determining the onset of the gesture (for example by looking at time differential of the power), then setting the threshold to be the value of previous point before the onset. Likewise, in some implementations the threshold value can be computed by a spectral clustering technique or other suitable clustering technique.

According to some aspects, the neuromuscular signals may be processed to generate a plurality of data points in a feature space. In some embodiments, vectorized covariances may be projected into or mapped to a tangent space of a manifold. For example, given a covariance matrix $C_i$ the vectorized covariances can be computed by:

$$S_i = \log(P^{-(1/2)} C_i P^{-(1/2)})$$

where P is a reference point, and can correspond, for example, to the identity matrix or the average covariance matrix computed from samples taken during users' rest or neutral positions. The symmetric square matrix $S_i$ has the same size as the covariance matrix. The vectorized covariances may be computed based on the upper diagonal part of the symmetric matrix $S_i$ for example, by keeping the upper triangular part of the symmetric matrix $S_i$ and vectorizing it by computing unity weights of the diagonal elements and squared root weights for out-of-diagonal elements.

The inventors have recognized that covariances and tangent space mapping provide a richer and more sensitive feature set than, for example, other features such as Mean Absolute Value (MAV) of an $i^{th}$ EMG channel computed over a time window, because MAV does not account for correlation between different EMG channels.

In some embodiments, an average covariance of the rest or neutral position data in the training data set may be used as the reference point, e.g., the zero of the tangent space. In some instances, a dimensionality reduction technique (e.g., Principal Component Analysis (PCA)) may be performed on the neuromuscular signals to generate the plurality of data points in the feature space. The PCA technique may be performed to compress the training data set while preserving data properties useful to differentiate between two or more gestures, and to generate an effective set of gesture features.

In some embodiments, the number of principal components (e.g., linearly uncorrelated variables) used in the PCA analysis may be arbitrarily set to the number of gestures to be identified by the system. Such a dimensionality reduction for training data set S can be denoted as $S=(x_1 \ldots, x_m)$, a feature mapping $\Phi: X \to \mathbb{R}^N$ and the data matrix $X \in \mathbb{R}^{N \times m}$ defined as $(\Phi(x_1), \ldots, \Phi(x_m))$, where the ith data point can be represented by $x_i = \Phi(x_1)$, or the ith column of X, which is an N-dimensional vector. Dimensionality reduction techniques such as PCA may be performed, for example, to find for k<<N, a k-dimensional representation of the data $Y \in \mathbb{R}^{k \times m}$, that correlates with the original representation of X.

The PCA may be computed by fixing $k \in [1, N]$ and letting X be a mean-centered data matrix, that is, $\Sigma_{i=1}^{m} x_i = 0$ and defining P as the set of N-dimensional rank-k orthogonal projection matrices. Thereafter, an N-dimensional input data can be projected onto a k-dimensional linear subspace that minimizes reconstruction error, e.g., the sum of the squared $L_2$-distances between the original data and the projected data. Accordingly, the PCA can be defined as the orthogonal projection matrix solution P* of the minimization of the error value computed as a function of the Frobenius norm F given by:

$$\min_{P \in P_k} \|PX - X\|_F^2$$

Figure 11:
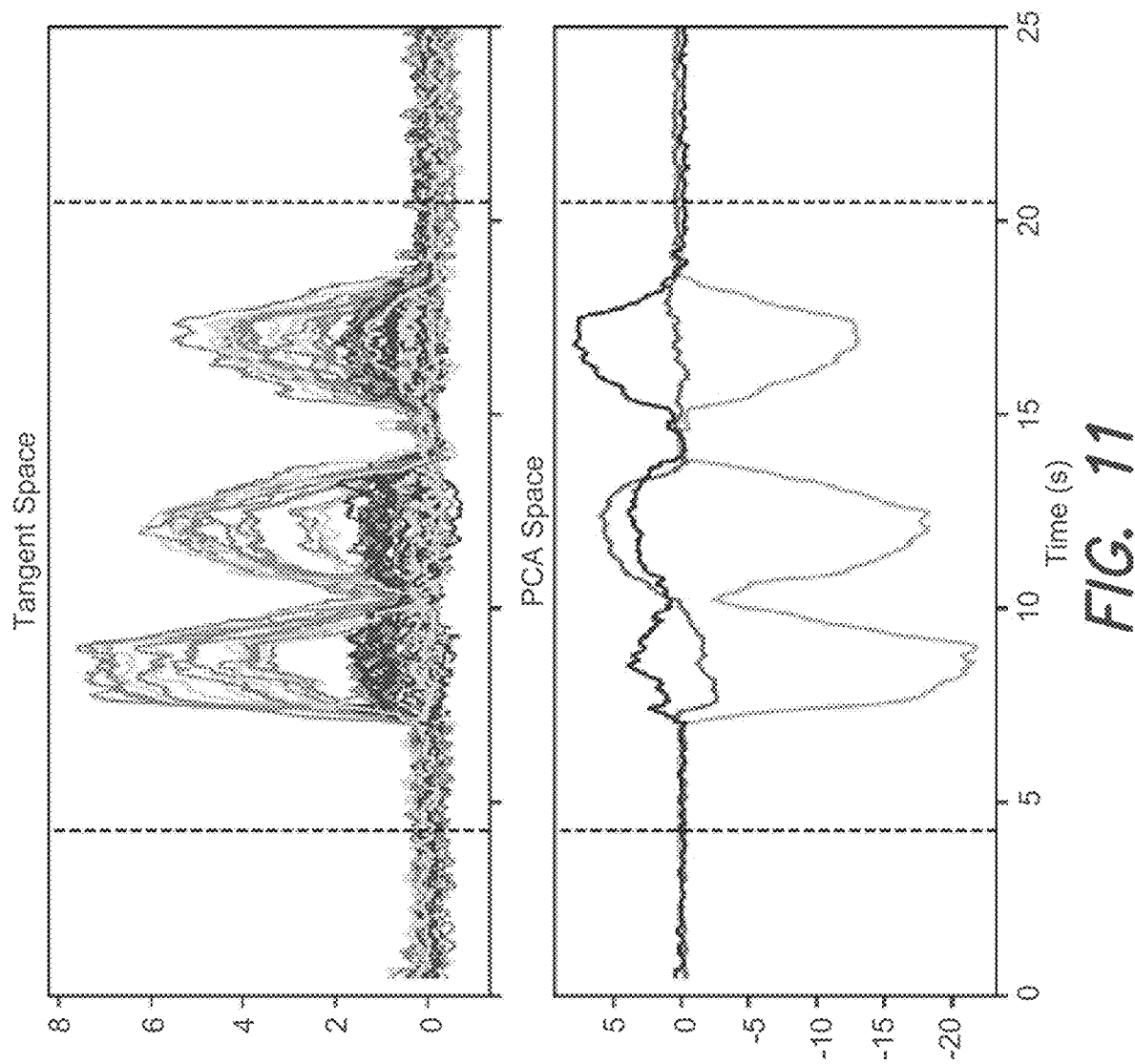
FIG. 11 illustrates a tangent space and a principal component analysis (PCA) space computed from a training data set, in accordance with some embodiments of the technology described herein.

FIG. 11 illustrates a computed tangent space (at the top portion of the figure) and a computed PCA feature space (at the bottom portion of the figure) of a pre-processed training data set. In the tangent space, a positive value denotes an increase in signal energy with respect to the rest/neutral position and a negative value denotes a decrease in signal energy with respect to the rest/neutral position. The application of the PCA technique produces a low-dimensional representation of the data sets as shown in the bottom portion of the figure (the sign is arbitrary in the PCA space). The PCA space shows sequence(s) of linear combinations of the variables that have maximal variance and are mutually uncorrelated.

According to some aspects, the plurality of data points generated in the feature space (e.g., the PCA feature space) may be clustered via a clustering technique to create a categorical representation of each of the performed gestures G1, G2, and G3. In some implementations, a K-means clustering technique may be used to partition the data points into a K number of clusters based on a similarity metric. It will be appreciated that in embodiments where the classification model is trained to recognize a single gesture, clustering of the data points may not be performed as it may be assumed that all data points correspond to a single cluster associated with the single gesture.

In some embodiments, the similarity among data points may be computed by identifying interrelations between different data points are interrelated, how data points are similar or dissimilar with each other, and determining a measure to compare similarities or regularities among data points (also referred herein as similarity metric). K-means defines a prototype in terms of a centroid, which is the mean of a group of points in a continuous n-dimensional space. A pseudocode representation of the K-means clustering technique is provided below:

1. Select K points as initial centroids.
2. repeat
3. Form k clusters by assigning all points to the closest centroid.
4. Recompute the centroid of each cluster.
5. until the centroids do not change The technique is initiated by selecting K initial centroids, where K is the number of desired clusters. Each data point is assigned to the nearest centroid, and each set of data points assigned to a centroid is considered a cluster. The centroid of a cluster may be updated several times based on the based on the data points assigned to the clusters. Step 3 (assignment) and step 4 (update) are repeated until no data point changes clusters, that is, until the centroids remain the same.

In some embodiments, a similarity metric used to partition EMG samples (data points) is based on the cosine distance between data points. The cosine distance is an example of suitable metric to distinguish between EMG samples that belong to the same gesture because each gesture can be characterized by a unique direction. Thus, EMG samples or data points that belong to the same gesture show a similar cosine distance between each other than data points that belong to a different gesture.

The K-means clustering technique is performed on the pre-processed training data set using the cosine distance as a similarity metric, excluding the data points corresponding to rest or neutral positions/gestures. After the K-means clustering technique is performed, the centroid of each cluster is stored or recorded to determine the directions of the feature space corresponding to each gesture.

Figure 12:
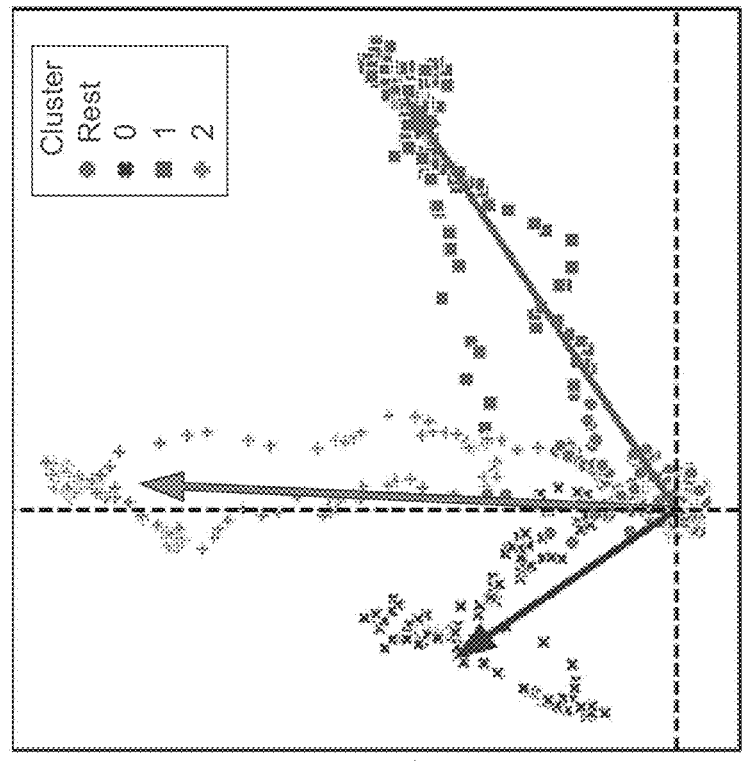
FIG. 12 illustrates examples of learned gesture vectors, in accordance with some embodiments of the technology described herein.
Figure 12:
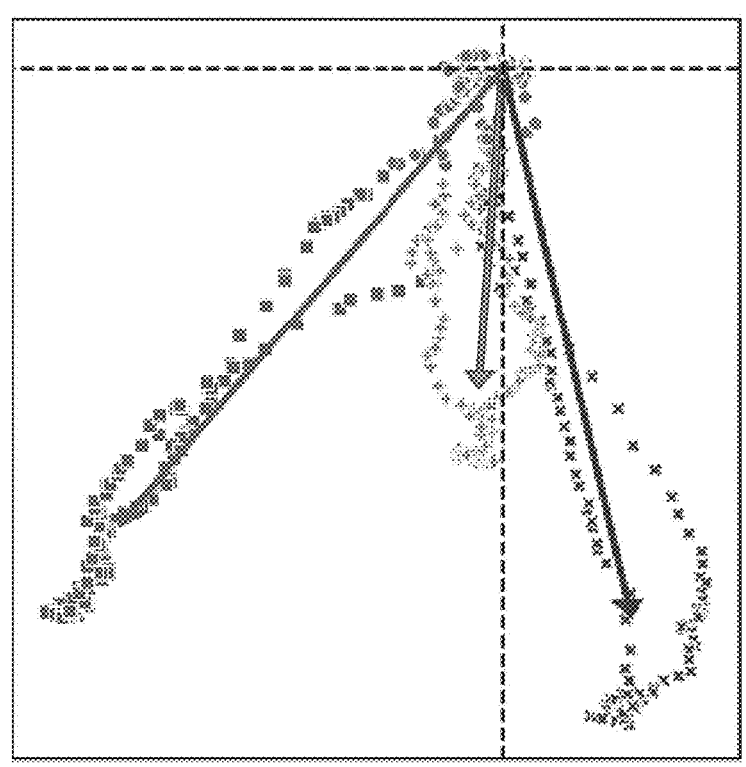

Clusters that share the same direction in the feature space may be effectively identified in part because they are represented as a single cluster. Thereafter, K directions or vectors $v_k$ can be determined (one vector per gesture as shown in FIG. 12, for example).

$v_k$ with $k \in [1:K]$ where K is the number of distinct gestures identified in the training phase.

Accordingly, for a given vector u of class y, class z can be determined by:

$$\hat{y} = \operatorname{argmin}_k \left(1 - \frac{(v_k, u)}{\|v_k\|\|u\|}\right)$$

the $\hat{f}$ of force f (i.e., force applied by the user during performance of a given gesture) is given by:

$$\hat{f} = \frac{(v_k, u)}{\|v_k\|^2}$$

FIG. 12 illustrates an example of a resulting plot after the application of the K-means clustering technique to the training data set on the three PCA principal components associated with gestures G1, G2, and G3. As shown, the different non-overlapping directions associated with each of the three clusters can be identified. Each gesture spans a unique direction in the feature space. If a gesture engages a set of muscles, increasing or decreasing the force applied while maintaining the gesture uniformly increases or decreases the contraction of each muscle in the engaged set of muscles. Accordingly, each arrow represents a gesture vector that conveys properties of the identified gesture including direction and force scale (e.g., a range of force values that the user can apply at the time of replicating the gesture or subsequently performing the gesture during the classification phase). A force level applied while performing a particular gesture may be defined by the magnitude of the gesture vector in a determined direction. In some embodiments, a gesture vector associated with a gesture represents a categorical representation of the gesture in the classification model.

Figure 13:
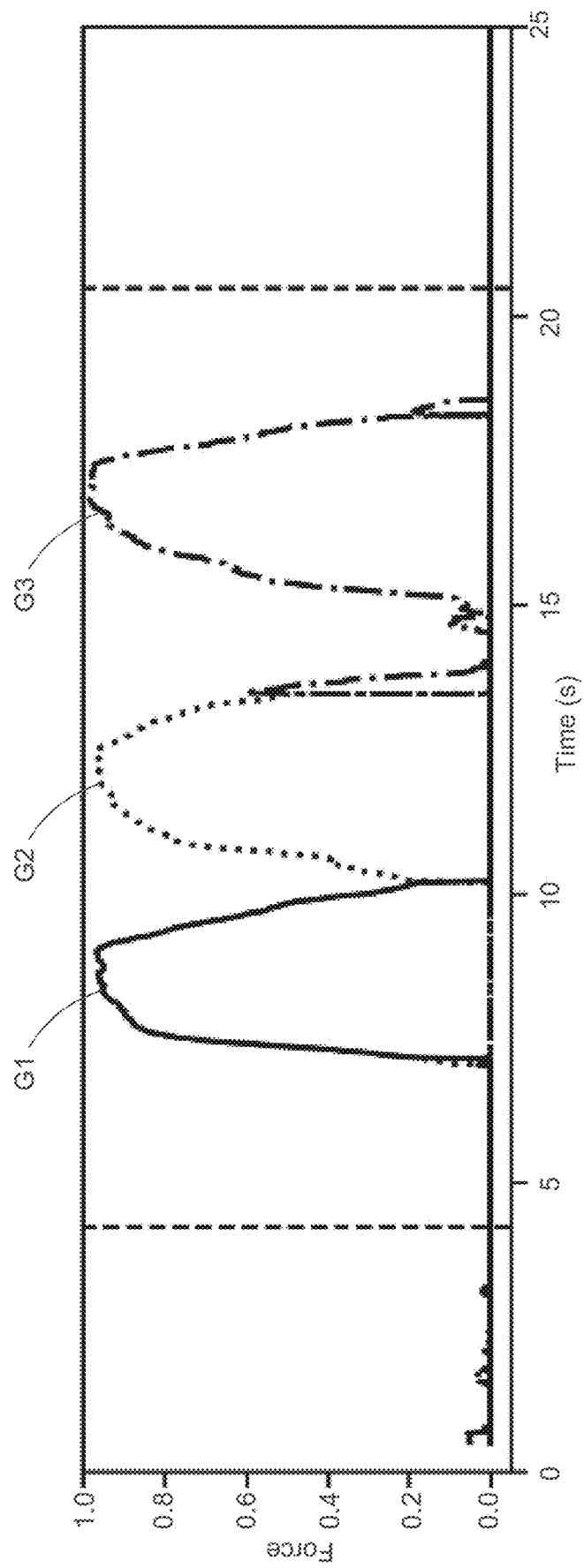
FIG. 13 illustrates a graph showing forces computed as a function of maximum voluntary contraction for each gesture performed during a training phase, in accordance with some embodiments of the technology described herein.

FIG. 13 illustrates the computed force associated with each of the gestures performed by the user during the training phase. In some embodiments, the computed force may be represented as a function of the Maximum Voluntary Contraction (MVC) for each of the three distinct gestures.

Example Technique for Recognizing a Gesture Based on the Trained Classification Model(s)—Gesture Recognition Phase After computing the direction and average magnitude corresponding to each of the gestures performed by the user during the training phase as discussed above, gesture classifications can be effectively determined for unseen gesture vectors. An unseen gesture vector is a vector derived from an unclassified user-defined gesture. As discussed below, unseen gestures can be classified when they correlate to gestures learned during the training phase and properties of such unseen gesture vector can be inferred including the force applied by the user while performing the unseen gesture. In some embodiments, the gesture vector for the unseen gesture may be generated in a manner similar to the generation of gesture vectors during the training phase.

Given an unseen gesture vector, a gesture can be inferred or classified based on a similarity metric (e.g., the cosine of the angle) between the unseen gesture vector and a set of gesture vectors produced during the training phase of the system. Each gesture vector in the set of gesture vectors corresponds to a gesture learned by the model during the training phase. For example, a match between an unseen gesture vector and a learned gesture vector can be inferred by selecting a learned gesture vector from the set of learned gesture vectors having the minimum cosine distance with respect to the unseen gesture vector. The force of the unseen gesture vector can be inferred by calculating the relative magnitude of the unseen gesture vector projected to the selected learned gesture vector (e.g., the learned gesture vector showing the smallest cosine distance with respect to the unseen gesture vector). Thus, the relative magnitude of the unseen gesture vector corresponds to the value of the scalar product between the unseen gesture vector and the selected learned gesture vector normalized by the magnitude of the selected learned gesture vector.

Figure 14:
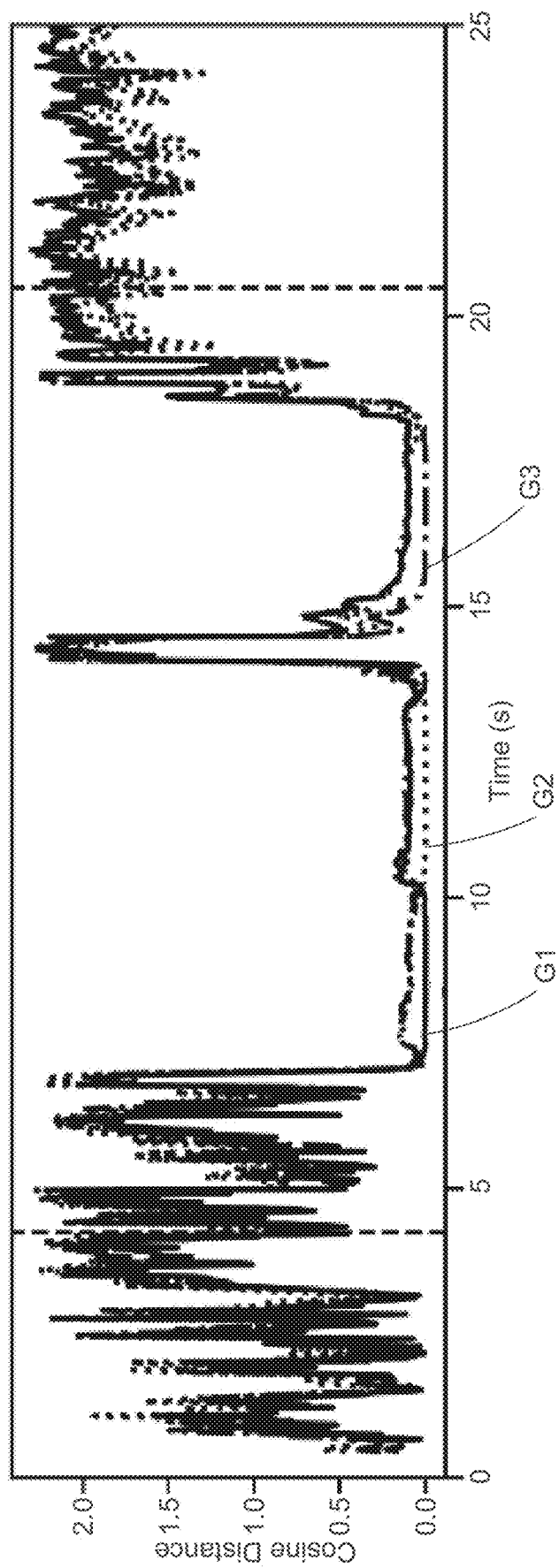
FIG. 14 illustrates identification of three different gestures based on their computed cosine distances, in accordance with some embodiments of the technology described herein.

Accordingly, unseen gesture vectors computed from subsequent user-performed gestures (after the training phase) can be classified, in some instances, based on their cosine distance. FIG. 14 shows the cosine distance between a learned gesture vector and an unseen gesture vector. The cosine distance between an unseen gesture vector and a learned gesture vector is closer to zero when the unseen gesture vector correlates to the learned gesture vector and diverges from zero when the unseen gesture vector does not correlate to a learned gesture vector. For example, FIG. 14 shows the cosine distances of three different unseen gesture vectors. In this instance, each of the three unseen gesture vectors matches a distinct learned gesture G1, G2, and G3.

In some other instances, an unseen gesture vector can correlate to a rest or neutral position and thus may be classified as a rest or neutral gesture. An unseen gesture vector can be classified as a rest or neutral gesture by determining whether the unseen gesture vector correlates to EMG signals taken while the user was in a rest or neutral position during the training phase. For example, if none of the distances between an unseen gesture vector and a learned gesture vector are lower than a predetermined threshold (e.g., 0.25 radians), it can be inferred that the unseen gesture vector corresponds to a rest or neutral position. Otherwise, the unseen gesture vector can be classified as a learned gesture vector that exhibits the minimum cosine distance with respect to the unseen gesture vector.

Figure 15:
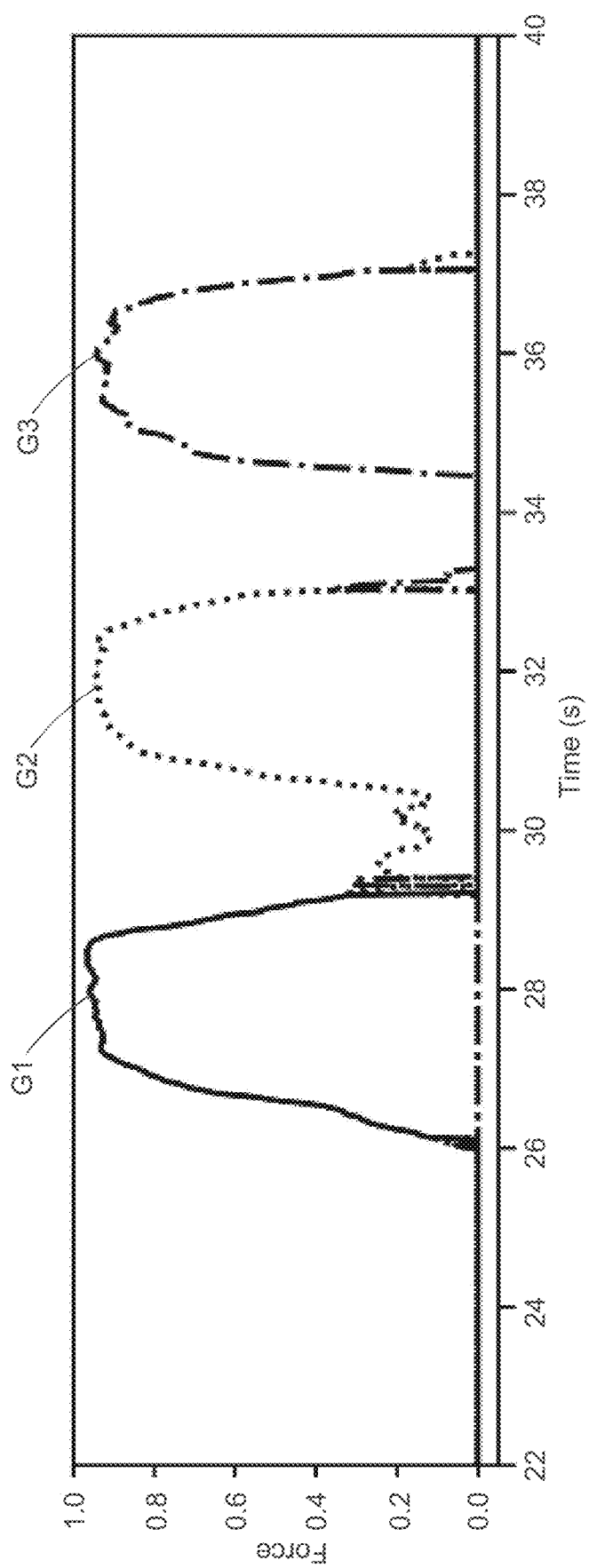
FIG. 15 illustrates forces inferred for each of the gestures identified during a classification phase, in accordance with some embodiments of the technology described herein.

As discussed above, the force associated with an unseen gesture vector can be inferred by computing the relative magnitude of the unseen gesture vector with respect to a learned gesture vector predicted to be correlated with the unseen gesture vector. FIG. 15 illustrates the forces inferred for each of the three identified gesture vectors.

Figure 16:
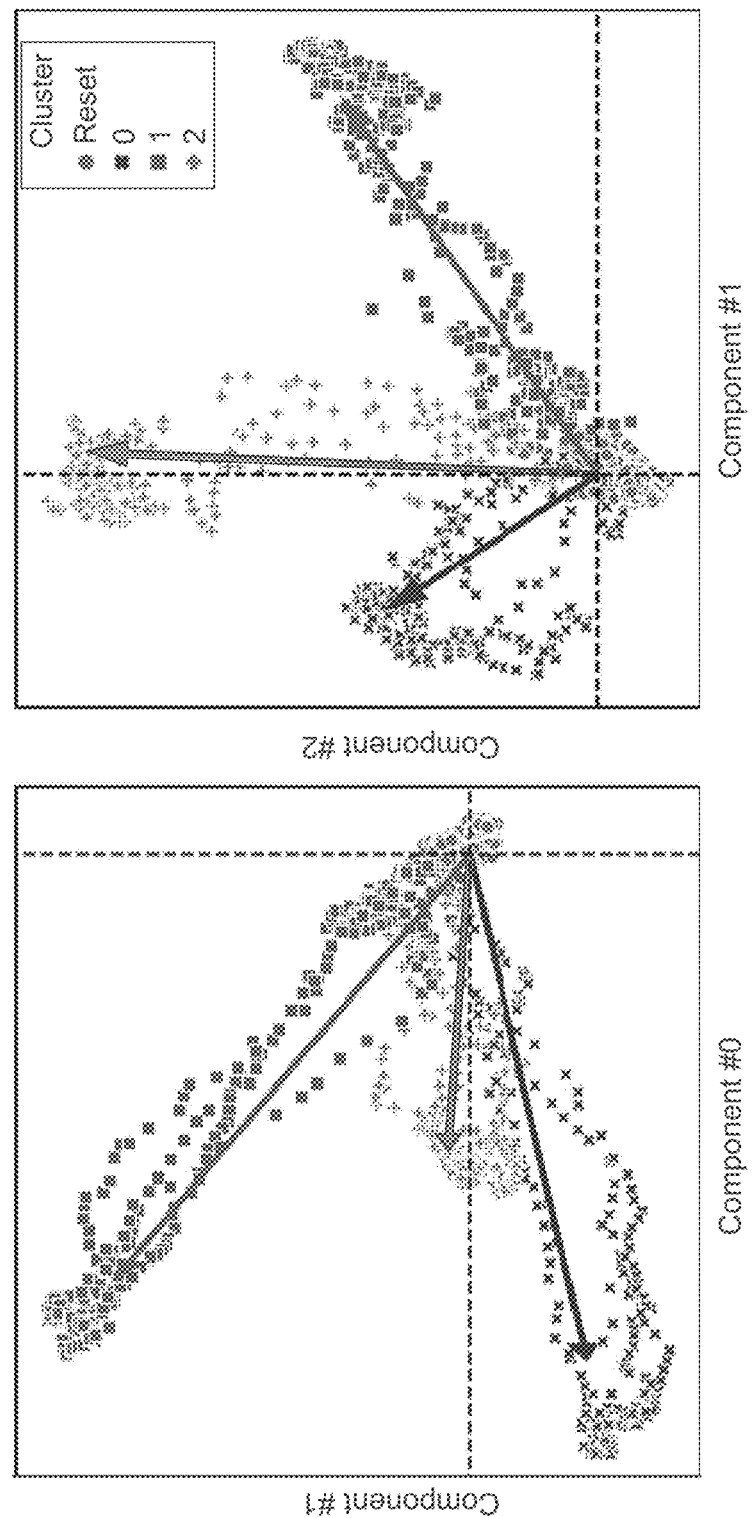
FIG. 16 illustrates three unseen vectors mapped to a Principal Components Analysis (PCA) space, in accordance with some embodiments of the technology described herein.

FIG. 16 illustrates the data maps on the PCA space of the unseen gesture vectors. It is appreciated that the directions of the learned gesture vectors illustrated in FIG. 12 remain strong predictive features even though the features were extracted from a single act of the gesture during the training phase.

Example Use Case with Wearable System

A user may wear the wearable system (e.g., wearable device depicted in FIG. 2A) having sixteen neuromuscular sensors. The user may perform K number of gestures, where K may be equal to one or any other number of gestures. The user may perform the gesture(s) for a certain period of time changing the force applied while performing each of the gesture(s). A classification model may be trained via an unsupervised machine learning approach to identify the performed gestures and generate a categorical representation of each of the identified gestures. The categorical representation may capture properties associated with the identified gesture (e.g., gesture type, an amount of force applied during performance of the gesture, etc.). The learned gesture(s) and/or forces may be mapped to a command/control signal such that each time the user performs a learned gesture(s), a control/command signal may be generated by the system. It will be appreciated that the training and use is not limited to the wearable system comprising an armband, and techniques described herein can be implemented with EMG sensors and/or other sensor arrangements different from the armband.

In some embodiments, the wearable system may be configured to generate one or more control signals when the user performs a user-defined gesture. Such a control signal may activate/deactivate compute devices, control objects in virtual environments, control objects in augmented reality environments, control IoT devices, and other suitable systems and/or devices. In some instances, a single gesture may be configured to generate different signals based on the force a user applies during performance of the gesture. For example, a first gesture performed by the user using a force below a threshold corresponding to half of the user's Maximum Voluntary Contraction (MVC) may cause the system to generate a signal to activate an electrical motor connected to a curtain or blind system causing the motor to close the curtains or blinds. Likewise, if the user performs a first gesture applying a force above or equal to the aforementioned threshold then, the system may generate a second signal configured to turn off the lights of the room in which the user is located. As another example, a gesture may be configured to control a signal such that the force applied during performance of the gesture is proportional to a property of the signal e.g., voltage, or other signal generated in an augmented or virtual reality environment. As yet another example, a gesture may be configured to control a dimmer or potentiometer to regulate the intensity of a light in a room to be proportional to the force the user applies during performance of the gesture.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. An apparatus, comprising:
a processor;
a plurality of neuromuscular sensors coupled to the processor; and
a memory storing instructions which, when executed by the processor, cause the processor to:
receive, via the plurality of neuromuscular sensors, a first plurality of neuromuscular signals from a user as the user performs a first single act of a gesture while changing an amount of force applied during performance of the gesture;

train a classification model using training data generated based on the first plurality of neuromuscular signals, the training data comprising data indicative of changes in the amount of force applied during performance of the gesture, wherein training the classification model comprises:
deriving, from the first plurality of neuromuscular signals, one or more values indicative of distinctive features of the gesture; and
generating a first categorical representation of the gesture in the classification model based on the one or more values derived from the first plurality of neuromuscular signals, wherein the first categorical representation characterizes the gesture that was performed using different amounts of force, and wherein different amounts of force detected from the neuromuscular signals are associated with different command signals capable of being sent to one or more connected devices, such that performance of the gesture with a detected force below a specified threshold is associated with a first command signal configured to control a first portion of functionality on the one or more connected devices, and performance of the gesture with a detected force above the specified threshold is associated with a second, different command signal configured to control a second, different portion of functionality on the one or more connected devices;
receive, via the plurality or neuromuscular sensors, a second plurality of neuromuscular signals from the user as the user performs a second single act of the gesture; and
determine that the user performed the second single act of the gesture based on the classification model and the second plurality of neuromuscular signals.

2. The apparatus of claim 1, wherein the first categorical representation of the gesture in the classification model is generated using an unsupervised machine learning technique.

3. The apparatus of claim 1, wherein the first categorical representation of the gesture comprises a vector in a feature space, the vector comprising a force scale indicative of force values associated with the different amounts of force applied during performance of the gesture.

4. The apparatus of claim 1, wherein the classification model is trained in near real-time.

5. The apparatus of claim 1, wherein the plurality of neuromuscular sensors are arranged on a wearable device.

6. The apparatus of claim 1, wherein the instructions, when executed by the processor, further cause the processor to:
determine at least one value indicative of a force applied by the user during performance of the second single act of the gesture.

7. The apparatus of claim 6, wherein the instructions, when executed by the processor, further cause the processor to:
in response to a determination that the at least one value indicative of a force applied by the user during performance of the second single act of the gesture exceeds a predetermined force threshold value, generating a first command signal to be communicated to a first connected device; and
in response to a determination that the at least one value indicative of the force applied by the user during performance of the second single act of the gesture does not exceed the predetermined force threshold value, generating a second command signal to be communicated to the first connected device, wherein the first command signal is different than the second command signal.

8. The apparatus of claim 6, wherein the instructions, when executed by the processor, further cause the processor to:
in response to a determination that at least one value indicative of a force applied by the user during performance of the second single act of the gesture exceeds a predetermined force threshold value, generating a first command signal to be communicated to a first connected device; and
in response to a determination that the at least one value indicative of the force applied by the user during performance of the second single act of the gesture does not exceed the predetermined force threshold value, generating a second command signal to be communicated to a second connected device, wherein the first connected device is different than the second connected device.

9. The apparatus of claim 1, wherein determining that the user performed the second single act of the gesture comprises:
deriving one or more second values from the second plurality of neuromuscular signals;
generating a second categorical representation of the gesture based on the derived one or more second values; and
determining that the user performed the second single act of the gesture based on a similarity metric computed between the first categorical representation of the gesture and the second categorical representation of the gesture.

10. The apparatus of claim 1, wherein the instructions, when executed by the processor, further cause the processor to:
determine an estimate of a force applied by the user during performance of the second single act of the gesture based on the first categorical representation of the gesture.

11. The apparatus of claim 1, wherein the instructions, when executed by the processor, further cause the processor to:
compute, based on the first categorical representation of the gesture, a sequence of values, each value from the sequence of values indicative of force applied by the user during performance of the second single act of the gesture, the sequence of values indicative of a change in force applied by the user during performance of the second single act of the gesture; and
generate at least one command signal to be communicated to a first connected device, wherein the at least one command signal is indicative of the change in force.

12. The apparatus of claim 1, wherein the instructions, when executed by the processor, further cause the processor to:
in response to the determination that the user performed the second single act of the gesture, generate a command signal to be communicated to a first connected device, the command signal configured to change an appearance of a graphical object displayed by the first connected device.

13. The apparatus of claim 1, wherein the instructions, when executed by the processor, further cause the processor to:

in response to the determination that the user performed the second single act of the gesture, generate a command signal to be communicated to a first connected device, the command signal configured to change a position of a graphical object displayed by the first connected device.

14. The apparatus of claim 1, wherein the instructions, when executed by the processor, further cause the processor to:
generate a command signal to be communicated to a first connected device, wherein the command signal is indicative of a number of times the user has performed the gesture.

15. An apparatus, comprising:
a processor;
a plurality of neuromuscular sensors coupled to the processor; and
a memory storing instructions which, when executed by the processor, cause the processor to:
train a classification model using training data generated based on a first plurality of neuromuscular signals and a second plurality of neuromuscular signals, the first plurality of neuromuscular signals and the second plurality of neuromuscular signals received via the plurality of neuromuscular sensors, the training data comprising data indicative of changes in an amount of force applied during performance of a first gesture and a second gesture, wherein the training comprises:
deriving, based on a clustering technique, a first set of values indicative of distinctive features of a first gesture and a second set of values indicative of distinctive features of a second gesture; and
generating a first categorical representation of the first gesture and a second categorical representation of the second gesture in the classification model, wherein:
the first categorical representation of the first gesture characterizes the first gesture that was performed using different amounts of force,
the second categorical representation of the second gesture characterizes the second gesture that was performed using different amounts of force, and
wherein the different amounts of force for the first and second gestures are associated with different command signals capable of being sent to one or more connected devices, such that performance of the gesture with a detected force below a specified threshold is associated with a first command signal configured to control a first portion of functionality on the one or more connected devices, and performance of the gesture with a detected force above the specified threshold is associated with a second, different command signal configured to control a second, different portion of functionality on the one or more connected devices, and
the categorical representation of the second gesture characterizes the second gesture that was performed using different amounts of force; and
determine, based at least in part on a third plurality of neuromuscular signals and the classification model, whether a user performed a subsequent act of the first gesture or the second gesture.

16. The apparatus of claim 15, wherein the first categorical representation of the first gesture and the second categorical representation of the second gesture are produced using one or more unsupervised machine learning technique.

17. The apparatus of claim 15, wherein the classification model is trained in near real-time.

18. The apparatus of claim 15, wherein the plurality of neuromuscular sensors are arranged in a wearable device.

19. The apparatus of claim 15, wherein:
the first categorical representation of the first gesture comprises a first vector in a feature space, the first vector comprising a force scale indicative of force values associated with the different amounts of force applied during performance of the first gesture, and
the second categorical representation of the second gesture comprises a second vector in a feature space, the second vector comprising a force scale indicative of force values associated with the different amounts of force applied during performance of the second gesture.

20. The apparatus of claim 15, wherein the instructions, when executed by the processor, further cause the processor to:
receive, via the plurality of neuromuscular sensors, the first plurality of neuromuscular signals from the user as the user performs a first single act of the first gesture while changing the amount of force applied during performance of the first gesture; and
receive, via the plurality of neuromuscular sensors, the second plurality of neuromuscular signals from the user as the user performs a first single act of the second gesture while changing the amount of force applied during performance of the second gesture.

21. The apparatus of claim 15, wherein the instructions, when executed by the processor, further cause the processor to:
determine a value indicative of a force applied by the user during performance of the subsequent act of the first gesture or a value indicative of a force applied by the user during performance of the subsequent act of the second gesture.

22. The apparatus of claim 15, wherein the instructions, when executed by the processor, further cause the processor to:
in response to a determination that the user performed a subsequent act of the first gesture, generate a first command signal to be communicated to a first connected device, wherein the first command signal includes a first force value indicative of a force applied during performance of the subsequent act of the first gesture; and
in response to a determination that the user performed a subsequent act of the second gesture, generate a second command signal to be communicated to the first connected device, wherein the second command signal includes a second force value indicative of a force applied during performance of the subsequent act of the second gesture, wherein the first command signal causes the first connected device to execute a different operation than the second command signal.

23. The apparatus of claim 15, wherein the instructions, when executed by the processor, further cause the processor to:
in response to a determination that the user performed a subsequence act of the first gesture, generate a first command signal to be communicated to a first connected device; and
in response to a determination that the user performed a subsequence act of the second gesture, generate a second command signal to be communicated to a second connected device, wherein the first connected device is different than the second connected device.

24. The apparatus of claim 15, wherein the instructions, when executed by the processor, further cause the processor to:
generate a plurality of signals to be communicated to a first connected device, each signal of the plurality of signals indicative of a subsequent act of the first gesture and a force value computed during performance of the subsequent act of the first gesture.

25. The apparatus of claim 15, wherein the instructions, when executed by the processor, further cause the processor to:
generate a plurality of signals to be communicated to a first or second connected device, each signal of the plurality of signals indicative of a subsequent act of the second gesture and a force value computed during performance of the subsequent act of the second gesture.

26. The apparatus of claim 15, wherein determining whether the user performed a subsequent act of the first gesture or the second gesture comprises:
deriving a third set of values from the third plurality of neuromuscular signals;
determining that the user performed a subsequent act of the first gesture based on a first similarity metric value computed between the third set of values and the first categorical representation of the first gesture; and
determining that the user performed a subsequent act of the second gesture based on a second similarity metric value computed between the third set of values and the second categorical representation of the second gesture.

27. A method, comprising:
receiving, at a processor of a wearable device, a plurality of neuromuscular signals from a plurality of neuromuscular sensors included in the wearable device, the plurality of neuromuscular signals corresponding to neuromuscular signals sampled from a user as the user performs a single act of a gesture while changing an amount of force applied during performance of the gesture;
training, via an unsupervised machine learning technique, a classification model using training data generated based on the neuromuscular signals associated with the single act of the gesture, wherein the training data comprises data indicative of changes in the amount of force applied during performance of the gesture, wherein the classification model comprises a first categorical representation of the gesture that characterizes the gesture that was performed using different amounts of force, and wherein different amounts of force detected from the neuromuscular signals are associated with different command signals capable of being sent to one or more connected devices, such that performance of the gesture with a detected force below a specified threshold is associated with a first command signal configured to control a first portion of functionality on the one or more connected devices, and performance of the gesture with a detected force above the specified threshold is associated with a second, different command signal configured to control a second, different portion of functionality on the one or more connected devices;
determining, based on the first categorical representation of the gesture, whether the user has performed a subsequent single act of the gesture;
determining at least one force value corresponding to a force applied by the user during performance of the subsequent single act of the gesture; and
generating a command signal to be communicated to the one or more connected devices in response to a determination that the user has performed the subsequent single act of the gesture.

28. The method of claim 27, wherein the classification model is trained in near real-time, and training the classification model via the unsupervised machine learning technique comprises:
generating the first categorical representation of the gesture in the classification model at least based on the plurality of neuromuscular signals, wherein the first categorical representation comprises a first vector in a feature space, the first vector comprising a force scale indicative of force values associated with the different amounts of force applied during performance of the single act of the gesture.

29. The method of claim 28, wherein the plurality of neuromuscular signals comprises a first plurality of neuromuscular signals, the gesture comprises a first gesture, and the method further comprises:
retraining the classification model, via the unsupervised machine learning technique, to determine whether the user performs a single act of a second gesture, wherein the first gesture is different than the second gesture, and the retraining comprises:
generating a second categorical representation of the second gesture in the classification model at least based on a second plurality of neuromuscular signals, the second categorical representation of the second gesture comprising a second vector in the feature space, the second vector comprising a force scale indicative of force values associated with different amounts of force applied during performance of the single act of the second gesture; and
determining, based on the classification model, whether a third plurality of neuromuscular signals correspond to a single act of the first gesture or to a single act of the second gesture.

30. The method of claim 27, wherein the command signal is indicative of the gesture and the at least one force value applied during performance of the gesture, and the command signal causes the device to execute an operation using the at least one force value as a parameter of the operation.

* * * * *